(12) United States Patent
Rauch et al.

(10) Patent No.: US 10,571,447 B2
(45) Date of Patent: Feb. 25, 2020

(54) FLUID FLOW SEPARATION CHAMBER FOR SEPARATING HYDROCARBONS FROM A FLUID, METHOD, AND SYSTEM OF USING THE SAME

(71) Applicants: Mark S. Rauch, Houston, TX (US); Ronald Kleineke, Mingo Junction, OH (US)

(72) Inventors: Mark S. Rauch, Houston, TX (US); Ronald Kleineke, Mingo Junction, OH (US)

(*) Notice: Subject to any disclaimer, the term of this patent is extended or adjusted under 35 U.S.C. 154(b) by 496 days.

(21) Appl. No.: 15/135,897

(22) Filed: Apr. 22, 2016

(65) Prior Publication Data

US 2016/0313293 A1    Oct. 27, 2016

Related U.S. Application Data

(60) Provisional application No. 62/259,947, filed on Nov. 25, 2015, provisional application No. 62/235,135, filed on Sep. 30, 2015, provisional application No. 62/174,423, filed on Jun. 11, 2015, provisional application No. 62/151,194, filed on Apr. 22, 2015.

(51) Int. Cl.
| | |
|---|---|
| *G01N 33/18* | (2006.01) |
| *G01N 33/28* | (2006.01) |
| *G01N 1/10* | (2006.01) |
| *B65D 88/38* | (2006.01) |

(52) U.S. Cl.
CPC ......... *G01N 33/1833* (2013.01); *B65D 88/38* (2013.01); *G01N 33/2835* (2013.01); *G01N 33/2847* (2013.01); *G01N 2001/1031* (2013.01); *Y02A 20/206* (2018.01)

(58) Field of Classification Search
CPC .................. G01N 33/1833; G01N 2001/1037
USPC .......................................................... 210/521
See application file for complete search history.

(56) References Cited

U.S. PATENT DOCUMENTS

| | | | |
|---|---|---|---|
| 1,902,108 A | 3/1933 | Twogood | |
| 2,826,306 A | 3/1958 | Burns | |
| 3,491,911 A | 1/1970 | Fraylick et al. | |
| 3,564,527 A * | 2/1971 | Lerner | G01M 3/40 340/605 |
| 4,022,694 A | 5/1977 | Fruman | |
| 4,128,833 A | 12/1978 | Tsavaris | |
| 4,134,833 A | 1/1979 | McCormick | |
| 4,202,366 A | 5/1980 | Kamvachirapitag | |
| 4,425,239 A | 1/1984 | Jacocks et al. | |

(Continued)

FOREIGN PATENT DOCUMENTS

| | | |
|---|---|---|
| CA | 2059830 C | 7/1993 |
| EP | 0885640 A1 | 12/1998 |

OTHER PUBLICATIONS

Extended European Search Report PCT/US2016028812 dated Mar. 5, 2019; 10 pages.

(Continued)

*Primary Examiner* — Nathaniel J Kolb
(74) *Attorney, Agent, or Firm* — BakerHostetler

(57) ABSTRACT

A monitoring system is configured to detect a threshold amount of petroleum in a storm water-based fluid of an oil handling facility. For instance, the storm water-based fluid can be drained from a floating roof of a petroleum storage tank, a diked area, or a retention pond.

21 Claims, 13 Drawing Sheets

(56) References Cited

U.S. PATENT DOCUMENTS

| | | | |
|---|---|---|---|
| 4,596,266 A * | 6/1986 | Kinghorn | B65D 88/38 |
| | | | 137/172 |
| 4,935,726 A * | 6/1990 | Buro | G01N 33/1833 |
| | | | 340/603 |
| 5,139,653 A * | 8/1992 | Ludlam | B01D 17/0214 |
| | | | 137/2 |
| 5,266,191 A * | 11/1993 | Greene | B01D 21/0039 |
| | | | 210/195.1 |
| 5,305,779 A | 4/1994 | Izaguirre | |
| 5,348,041 A * | 9/1994 | Clark | B01D 17/0208 |
| | | | 137/172 |
| 5,484,522 A | 1/1996 | Entrekin | |
| 5,862,996 A | 1/1999 | Crichton | |
| 5,935,427 A | 8/1999 | Witter et al. | |
| 6,456,197 B1 | 9/2002 | Lauritsen et al. | |
| 6,810,365 B1 * | 10/2004 | Brown | B01D 19/0063 |
| | | | 210/93 |
| 7,041,213 B1 * | 5/2006 | McClanahan | E03F 5/18 |
| | | | 210/100 |
| 7,227,139 B2 | 6/2007 | Kram et al. | |
| 7,688,428 B2 * | 3/2010 | Pearlman | G01J 3/02 |
| | | | 356/70 |
| 7,862,730 B2 | 1/2011 | McEwen et al. | |
| 8,820,182 B2 | 9/2014 | Nikolay Nikolov et al. | |
| 2005/0161397 A1 | 7/2005 | Hanks | |
| 2005/0189294 A1 | 9/2005 | Prenger et al. | |
| 2007/0210262 A1 * | 9/2007 | Pearlman | G01J 3/02 |
| | | | 250/461.1 |
| 2009/0184049 A1 | 7/2009 | Murray et al. | |
| 2010/0200514 A1 * | 8/2010 | Crocker | C02F 1/004 |
| | | | 210/741 |
| 2014/0216998 A1 | 8/2014 | Al-Hadhrami et al. | |
| 2014/0231094 A1 | 8/2014 | Greci | |

OTHER PUBLICATIONS

Written Opinion of the International Searching Authority for PCT/US2017/058079 dated Feb. 9, 2018; 11 pages.

* cited by examiner

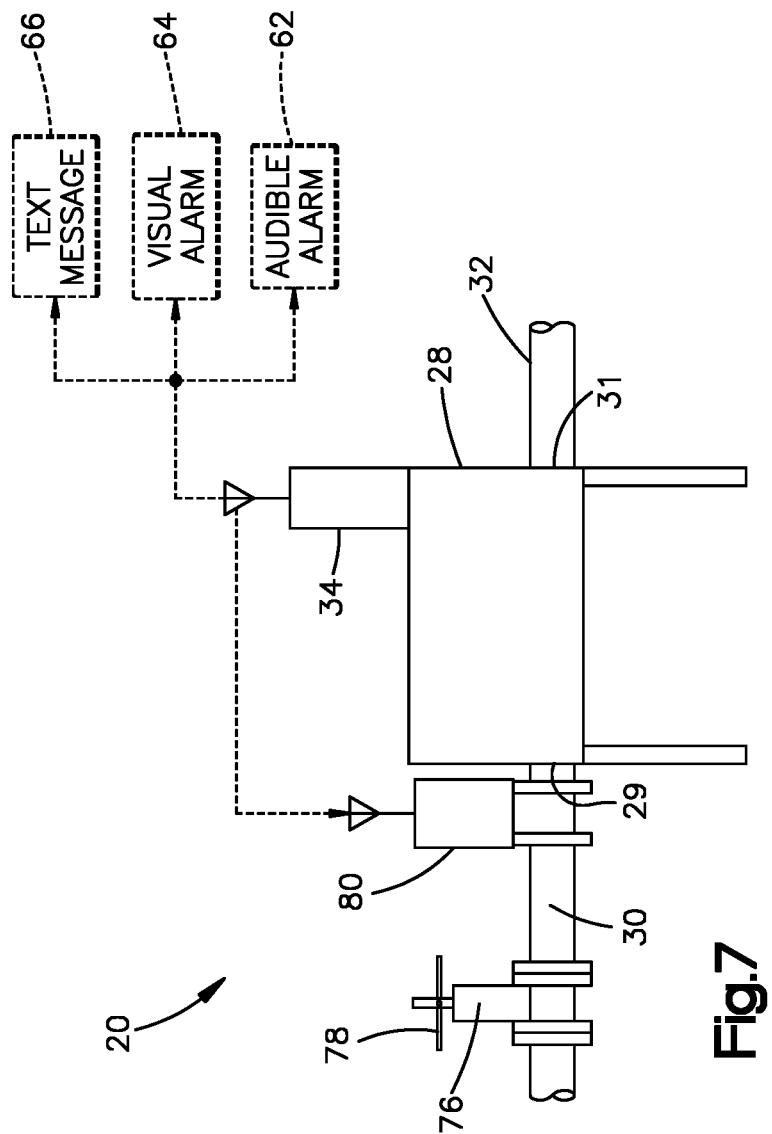

FLUID FLOW SEPARATION CHAMBER FOR SEPARATING HYDROCARBONS FROM A FLUID, METHOD, AND SYSTEM OF USING THE SAME

CROSS-REFERENCE TO RELATED APPLICATIONS

This claims the benefit of U.S. Provisional Patent Application Ser. No. 62/259,947 filed on Nov. 25, 2015, U.S. Provisional Patent Application Ser. No. 62/235,135 filed on Sep. 30, 2015, U.S. Provisional Patent Application Ser. No. 62/174,423 filed on Jun. 11, 2015, and U.S. Provisional Patent Application Ser. No. 62/151,194 filed on Apr. 22, 2015, the disclosure of each of which is hereby incorporated by reference as if set forth in its entirety herein.

BACKGROUND

Referring to FIGS. 1A-1C, oil handling facilities 10, such as petroleum storage facilities 12, petroleum processing facilities 14 such as oil refineries 15, and oil mining facilities 19 such as oil wells 17, and the like, are typically disposed in containment areas 16 that are designed to contain liquids that become contaminated with hydrocarbons. For instance, oil handling facilities can be susceptible to storm water, either in the form of run off or accumulation on the storage tanks. The storm water that runs off from oil handling facilities can become contaminated with hydrocarbons. The containment areas 16 are designed to contain the storm water run off, thereby preventing the possibility of contaminants in the run off from entering the ambient environment outside the containment area 16. Alternatively or additionally, oil handling facilities 10 can also include run off retention ponds that are configured to receive and store storm water run off.

Further, petroleum storage tanks are available with floating roofs that rest atop the petroleum stored in the tank, and thus rises and falls with increasing and decreasing levels of petroleum. Floating roofs are conventionally employed as a way to safely store the contained petroleum with minimal escape of petroleum vapors into the environment. The floating roof is sealed with respect to the outer tank wall, such that as the volume of stored petroleum changes, the floating roof slides along the side wall of the tank without allowing leakage at the interface of the floating roof and the side wall of the tank. It is recognized that the floating roof and the portion of the side wall of the tank that resides above the floating roof can cooperate to define a basin that collects storm water. If the collected storm water is allowed to remain, the volume of storm water can collect in an amount sufficient to compromise the structural integrity of the roof.

Whether it is desired to discharge the storm water that is present in the form of run off in a retention pond, or present in the form of storm water collected by the roofs of petroleum storage tanks, it is desirable to discharge the storm water to a remote location outside the oil handling facility, where it can enter the environment outside the containment area 16. However, it is desirable to ensure that environmentally harmful oil has not contaminated the storm water prior to discharging the storm water into the environment.

SUMMARY

The following Summary is provided to introduce a selection of concepts in a simplified form that are further described below in the Detailed Description. This Summary is not intended to identify key features or essential features of the invention, nor is it intended to be used to limit the scope of the invention. Reference is made to the claims for that purpose.

In one aspect of the present disclosure, a method is provided for monitoring for a presence of hydrocarbons among group of hydrocarbons in a fluid discharged from a location of an oil handling facility, the group of hydrocarbons including diesel/fuel oil, lube oil, motor oil, hydraulic oil, jet fuel, mineral oil, and crude oil. The method can include the step of directing a fluid from the location of the oil handling facility and into a fluid flow separation chamber. The method can further include the step of causing the fluid to flow from an inlet of the fluid flow separation chamber to an outlet of the fluid flow separation chamber. The method can further include the step of sensing the fluid proximate to the outlet of the fluid flow separation chamber for the presence of the hydrocarbons. When the sensing step detects the presence of a threshold amount of the hydrocarbons in the fluid, the method can further include the step of closing a valve at a location between the roof and the outlet of the fluid flow separation chamber, thereby preventing further flow of the fluid from the floating roof to the outlet of the fluid flow separation chamber.

In another aspect of the present disclosure, a method is provided for assembling a monitoring system for a floating roof petroleum storage tank. The method can include the step of installing a valve in a first conduit that extends between a drain in the floating roof and a location external of the storage tank, wherein the valve is configured to selectively permit and prevent fluid from flowing through the first conduit past the valve. The method can further include the step of attaching the first conduit to an inlet of a fluid flow separation chamber having an outer housing that includes a base, outer wall that extends from the base along a transverse direction, and a plurality of baffles that define 1) respective channels oriented in a select direction perpendicular to the transverse direction so as to direct fluid to flow in the select direction, and 2) respective gaps at least partially defined by the baffles. The method can include the step of placing a sensor in operative communication with an interior of the fluid flow separation chamber at a location proximate to an outlet of the fluid flow separation chamber that is opposite the inlet, such that the sensor is configured to sense a presence of petroleum at the location proximate to the outlet.

In another aspect of the present disclosure, a method can be provided for assembling a monitoring system for a location of an oil handling facility including at least one of a petroleum storage facility, an oil processing facility, and an oil mining facility. The method can include the step of installing a valve in a first conduit that extends from a drain that is open to the location, wherein the valve is configured to selectively permit and prevent fluid from flowing through the first conduit past the valve. The method can further include the step of attaching the first conduit to an inlet of a fluid flow separation chamber having an outer housing that includes a base, outer wall that extends from the base along a transverse direction, and a plurality of baffles that define 1) respective channels oriented in a select direction perpendicular to the transverse direction so as to direct fluid to flow in the select direction, and 2) respective gaps at least partially defined by the baffles. The method can include the step of placing a sensor in operative communication with an interior of the fluid flow separation chamber at a location proximate to an outlet of the fluid flow separation chamber that is opposite the inlet, such that the sensor is configured to sense a presence of hydrocarbons at the location proximate to the outlet, wherein the hydrocarbons are among a group of hydrocarbons that includes diesel/fuel oil, lube oil, motor oil, hydraulic oil, jet fuel, mineral oil, and crude oil.

In another aspect of the present disclosure, a fluid flow separation chamber can be configured to cause petroleum in a fluid to rise to an upper surface of the fluid. The fluid flow separation chamber can include a chamber body having a base, and an outer wall that extends up from the base. The fluid flow separation chamber can further include a plurality of baffles that extend up from the base, such that adjacent ones of the baffles define respective fluid flow channels, wherein each of the plurality of baffles extends from the one outer wall at a first end, and define a respective gap at a second end opposite the first end, such that the gaps are aligned with each other along a plane that is parallel to the base. The fluid flow separation chamber can further include an inlet that extends through the body, wherein the fluid flow separation chamber is configured to receive the fluid through the inlet. The fluid flow separation chamber can further include an outlet that extends through the at body at a location downstream of the inlet with respect to the direction of fluid flow through the fluid flow separation chamber, wherein the fluid flow separation chamber is configured to expel the fluid through the outlet.

In another aspect of the present disclosure, a monitoring system can include the fluid flow separation chamber as described above, and a hydrocarbon sensor disposed proximate to the outlet of the fluid flow separation chamber, wherein the hydrocarbon sensor is configured to output a signal in response to a detection of a threshold amount of hydrocarbons of a group of hydrocarbons present in a fluid that travels through the fluid flow separation chamber along a direction from the inlet to the outlet, wherein the group of hydrocarbons includes diesel/fuel oil, lube oil, motor oil, hydraulic oil, jet fuel, mineral oil, and crude oil.

BRIEF DESCRIPTION OF THE DRAWINGS

The foregoing summary, as well as the following detailed description, is better understood when read in conjunction with the appended drawings. There is shown in the drawings example embodiments, in which like reference numerals correspond to like reference numerals throughout. The present invention is not intended to be limited to the specific embodiments and methods disclosed, and reference is made to the claims for that purpose.

FIG. 7 is a schematic diagram illustrating communications operations of the monitoring system illustrated in FIG. 4;

DETAILED DESCRIPTION

Figure 1A:
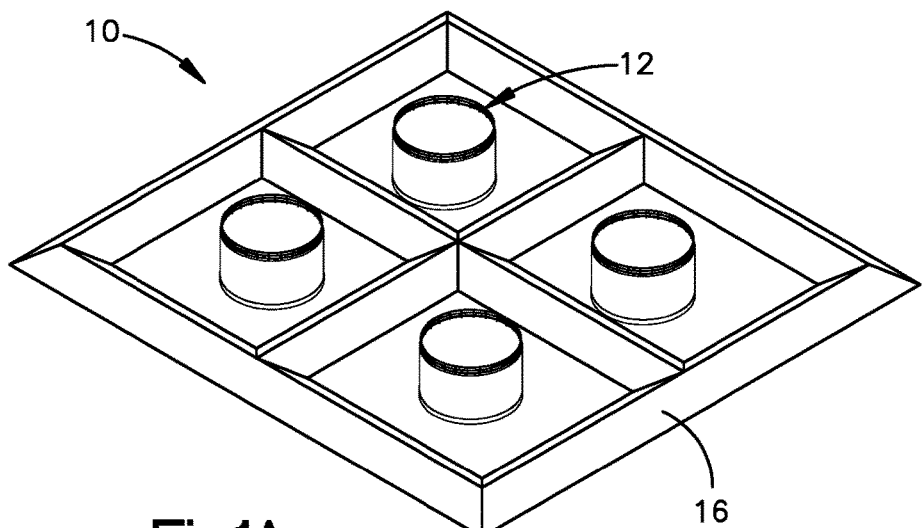
FIG. 1A is a schematic perspective view of a conventional petroleum storage facility.
Figure 1B:
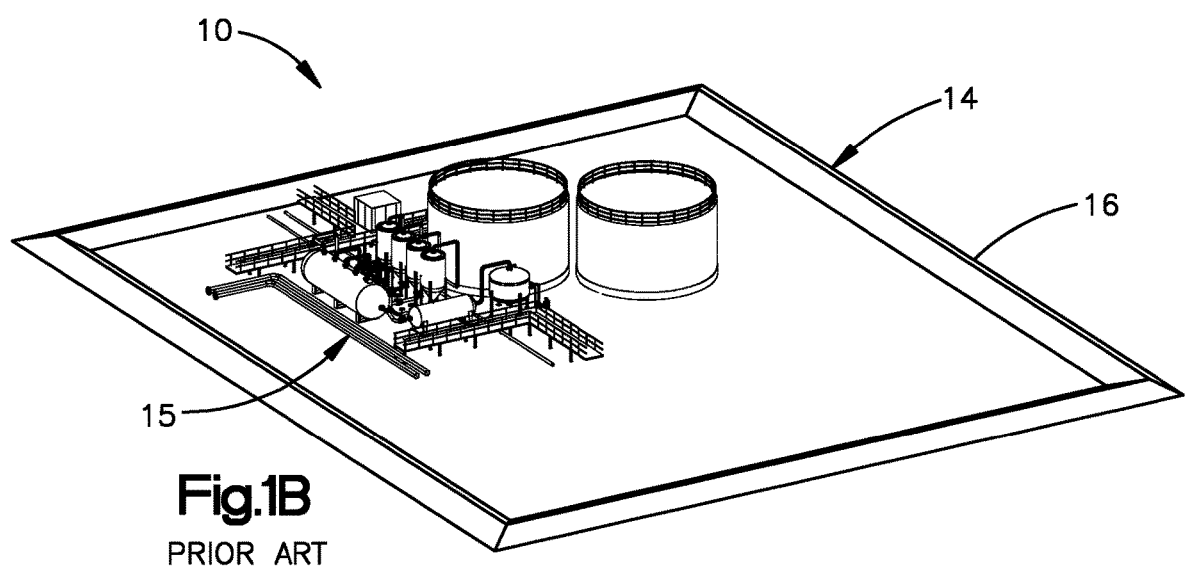
FIG. 1B is a schematic perspective view of a conventional petroleum processing facility.
Figure 1C:
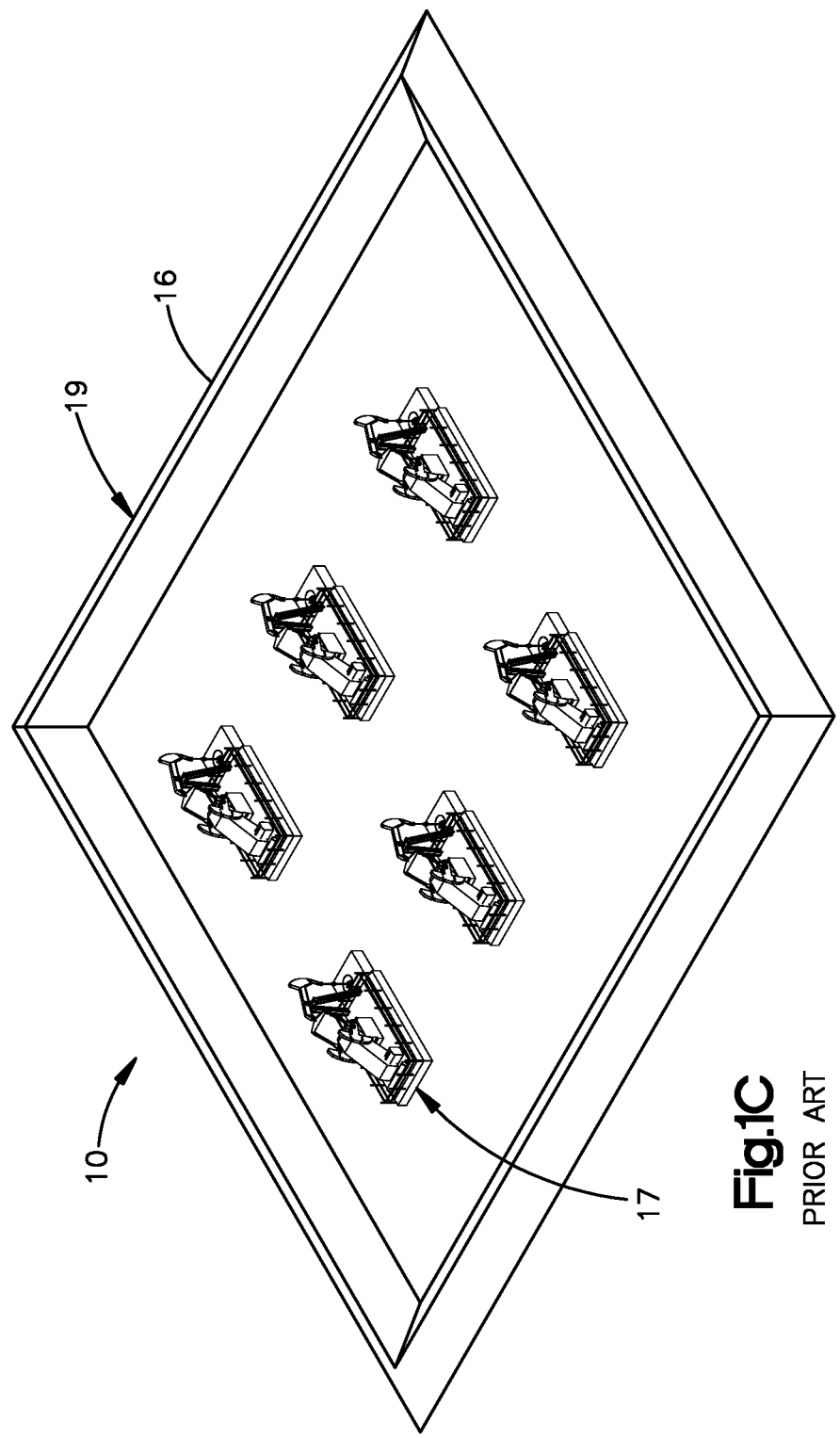
FIG. 1C is a schematic perspective view of a conventional oil mining facility.
Figure 2:
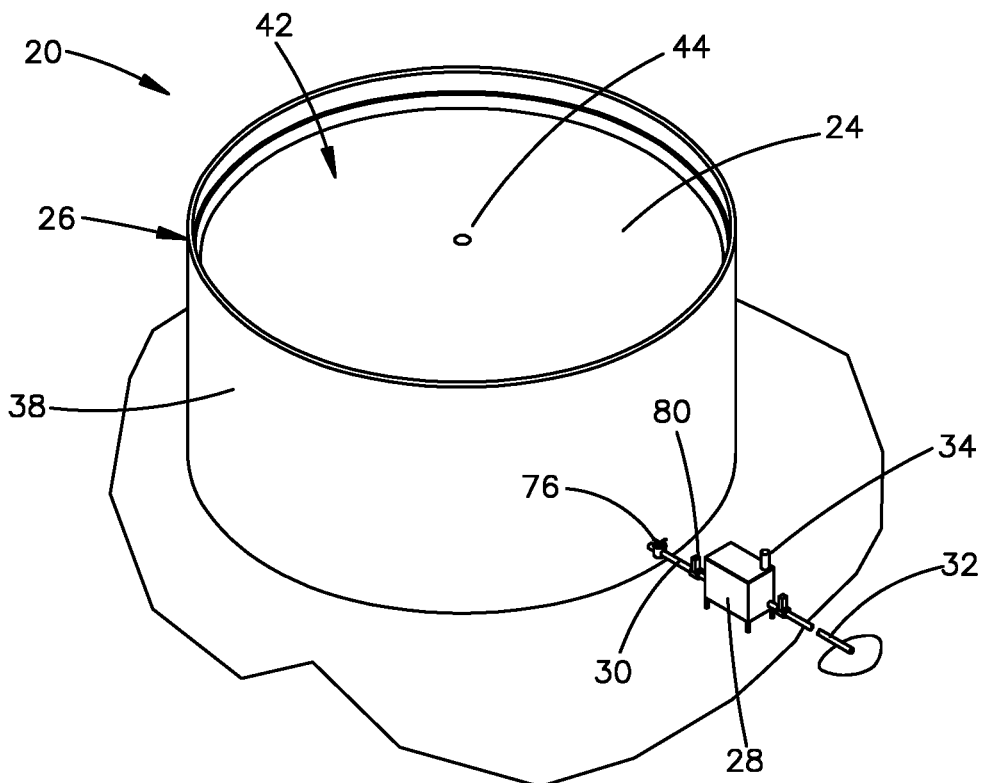
FIG. 2 is a perspective view of a monitored petroleum storage assembly including a petroleum storage tank and a monitoring system.
Figure 3A:
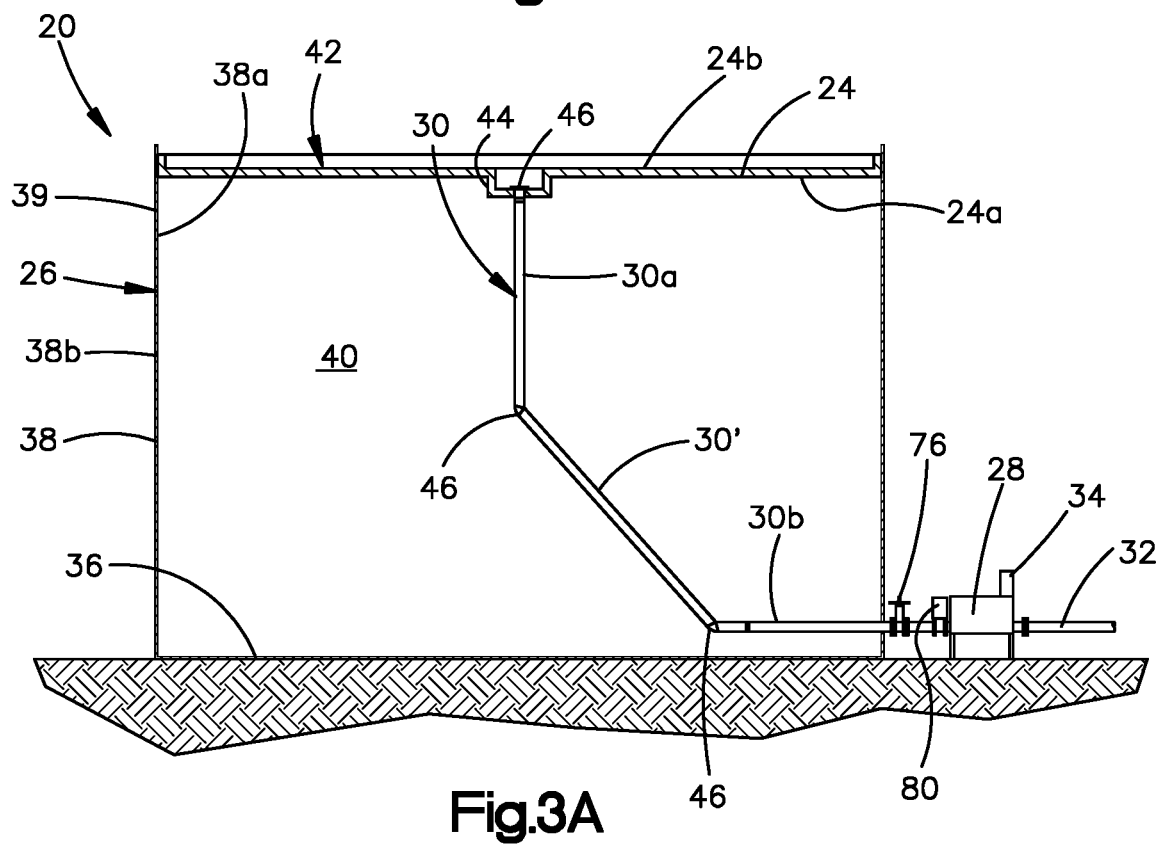
FIG. 3A is a side elevation view of the monitored petroleum storage assembly illustrated in FIG. 2, showing an interior of the petroleum storage tank having a floating roof at a first elevation.
Figure 3B:
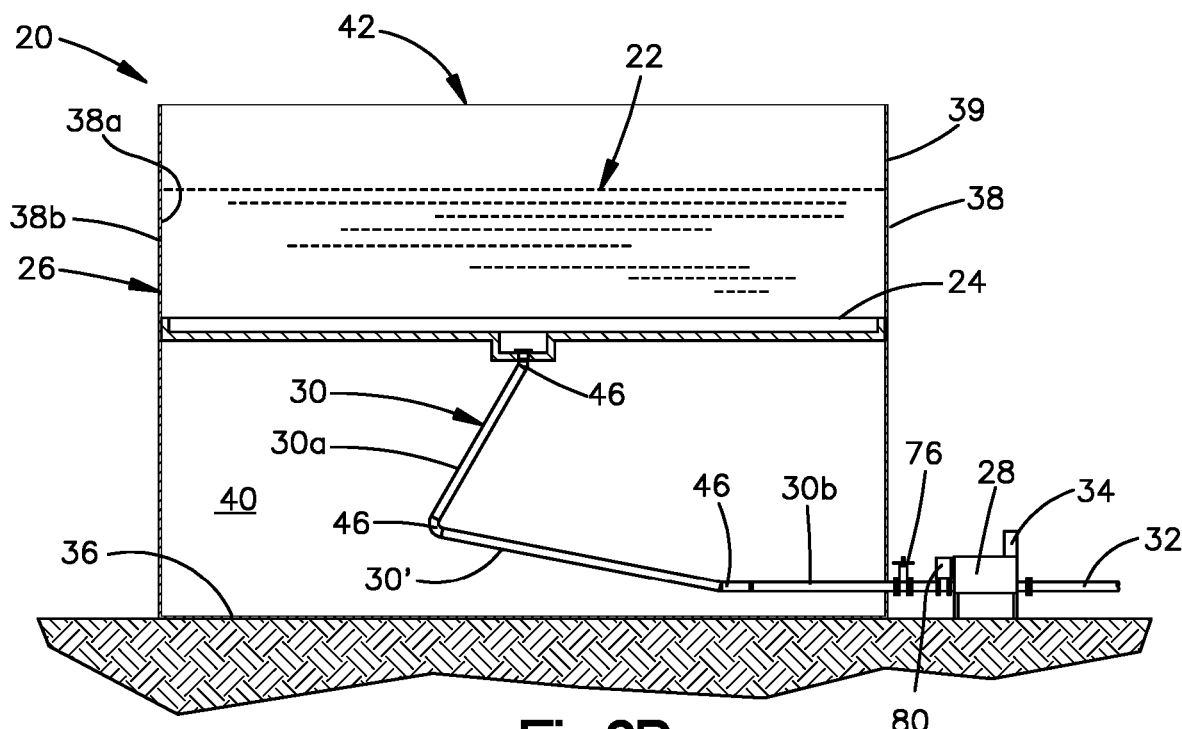
FIG. 3B is a side elevation view of the monitored petroleum storage assembly illustrated in FIG. 3A, but showing the floating roof at a second elevation different than the first elevation.
Figure 4:
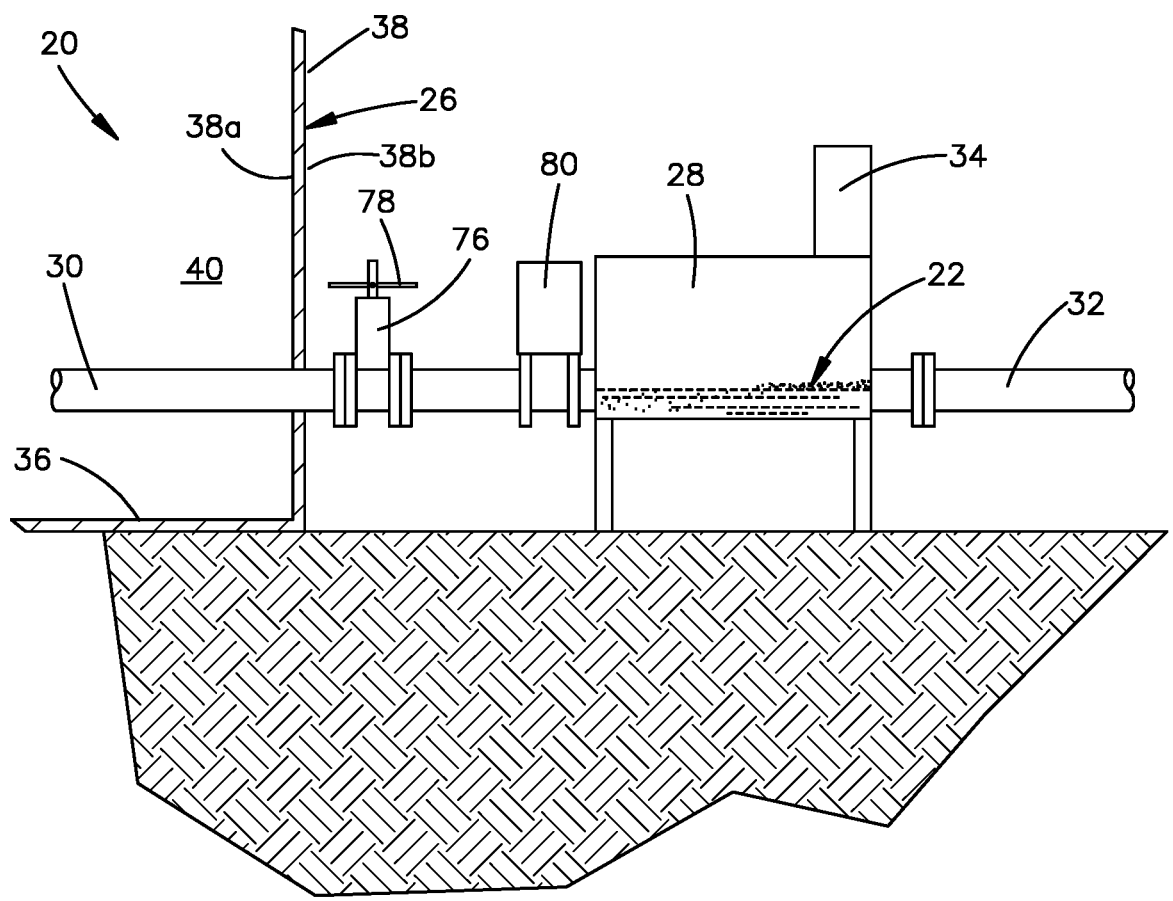
FIG. 4 is a schematic side view of the monitoring system illustrated in FIG. 2, shown constructed in accordance with one embodiment.

Referring to FIGS. 2-4, a monitoring system 20 is configured to detect the presence of a selected group of hydrocarbons in a fluid 22 to be discharged from a location of an oil handling facility. The selected group of hydrocarbons can include diesel/fuel oil, lube oil, motor oil, hydraulic oil, jet fuel, mineral oil, and crude oil. Thus, reference herein to hydrocarbons refers to the selected group of hydrocarbons unless otherwise indicated. The oil handling facility can be in the form of a petroleum storage facility 23 (see FIG. 11A), an oil processing facility 25 (see FIG. 11B), or an oil mining facility 33 (see FIG. 11C). Thus, the location of the oil handling facility can be a floating roof of a petroleum storage tank, or a retention pond of an oil processing facility or oil mining facility. While the monitoring system will now be described in conjunction with a petroleum storage facility, it will be appreciated from the description below that the monitoring system can be used in conjunction with an oil processing facility or an oil mining facility.

The petroleum storage facility 23 includes at least one petroleum storage tank 26 such as a plurality of petroleum storage tanks 26 that each has a floating roof 24. Thus, the discharged fluid 22 to be monitored can be drained from a floating roof 24 of the and out the petroleum storage tank 26. The petroleum storage tank 26 can be dimensioned to store any suitable volume of petroleum as desired, from several hundred thousands of gallons of petroleum to several million gallons of petroleum. The fluid 22 can be a storm water-based fluid.

The monitoring system 20 can include one or more up to all of the oil handling facility, a fluid flow separation chamber 28, and first or an inlet conduit 30 that extends from the oil handling facility to an inlet 29 (see FIG. 5A) of the fluid flow separation chamber 28, and a hydrocarbon sensor 34 that is configured to be supported by the fluid flow separation chamber 28. When the oil handling facility includes the petroleum storage tank 26, the outlet conduit 30 extends from the petroleum storage tank 26 to the inlet 29, and is configured to deliver fluid 22 that is discharged from the petroleum storage tank 26 to the fluid flow separation chamber 28. The monitoring system 20 can further include a heater 81 that is configured to deliver heat to the inlet conduit 30, thereby preventing the fluid from freezing in the inlet conduit 30 during periods of cold weather. The monitoring system 20 can further include a second or outlet conduit 32 having a first end attached to an outlet 31 (see FIG. 5A) of the fluid flow separation chamber 28, and a second end configured to deliver the fluid 22 to a location in the environment, such as the earth. The outlet conduit 32 can define an inner cross-sectional area such as an inner diameter that is greater than that of the inlet conduit 30. In one example, the outlet conduit 32 can have an inner diameter of five inches or greater (such as between 5 inches and 10 inches), and the inlet conduit 30 can have an inner diameter of less than five inches (such as between 2 inches and 5 inches), though it should be appreciated that the inner diameters of the inlet conduit 30 and the outlet conduit 32 can be alternatively dimensioned as desired. It should be further appreciated that the size of the separation chamber 28 and conduits can be scaled up or down depending on the volume of fluid 22 that is expected to be received by the fluid flow separation chamber 28 in a given application.

It is recognized that seals can wear, and other conditions can allow quantities of petroleum of the storage tank 26 to enter the inlet conduit 30. In order to prevent the delivery of the fluid 22 to the ambient environment outside the containment area when the fluid 22 contains a predetermined threshold amount of petroleum, the monitoring system 20 can include a hydrocarbon sensor 34 that is configured to detect the threshold amount of hydrocarbons in the fluid 22 at a location inside the fluid flow separation chamber 28. When the oil handling facility is configured as a petroleum storage facility, the hydrocarbons can, for instance, be present in petroleum that has entered the fluid 22 from the storage tank 26. In this regard, the hydrocarbon sensor 34 can be referred to as a petroleum sensor, and the monitoring system 20 can be referred to as a petroleum monitoring system. As will be described in more detail below, the fluid flow separation chamber 28 is configured to cause hydrocarbons present in the fluid 22 to rise to the upper surface of the fluid 22 to create a sheen, such that it can be reliably detected by the hydrocarbon sensor 34. Further, as described in more detail below, the monitoring system 20 can prevent the delivery of the fluid 22 into the environment when the hydrocarbon sensor 34 detects the predetermined threshold amount of petroleum in the fluid 22. The threshold amount can be any amount of petroleum in the fluid 22 that is greater than zero. For instance, the threshold amount can be any amount of petroleum that produces a sheen on an upper surface of the fluid 22. The hydrocarbon sensor 34 can be constructed as described in U.S. Pat. No. 7,688,428, the disclosure of which is hereby incorporated by reference as if set forth in its entirety herein. It should be appreciated, of course, that the hydrocarbon sensor 34 can be constructed in accordance with any alternative embodiment as desired, suitable to detect petroleum present in a fluid.

As illustrated in FIGS. 2-3B, the petroleum storage tank 26 can include a base 36, and at least one side wall 38 that extends up from the base 36. The side wall 38 can define an inner surface 38a and an outer surface 38b opposite the inner surface. The inner surface 38a can at least partially define an interior 40 of the storage tank 26 that is configured to house a quantity of petroleum. For instance, the base 36, the side wall 38, and the floating roof 24 can cooperate so as to define the interior 40 of the storage tank 26. The at least one side wall 38 can be configured as a cylindrical wall, or can define any suitable alternative shape as desired.

The floating roof 24 defines a lower surface 24a and an upper surface 24b opposite the lower surface 24a. The lower surface 24a is configured to face the interior 40 of the storage tank 26. As the volume of petroleum stored in the interior 40 of the storage tank 26 increases, the floating roof 24 rises with respect to the at least one side wall 38. Similarly, as the volume of petroleum stored in the interior 40 of the storage tank 26 decreases, the floating roof 24 falls with respect to the at least one side wall 38. For instance, the floating roof 24 can ride along the inner surface 38a of the at least one side wall 38 as the floating roof 24 rises and falls. The floating roof 24 can be sealed against the inner surface 38a of the side wall 38 so as to prevent the leakage of petroleum through the interface between the floating roof 24 and the inner surface 38a of the side wall 38, and into the environment. Further the sealed interface between the floating roof 24 and the inner surface 38a of the side wall 38 can prevent environmental contaminants from entering the interior 40 of the petroleum storage tank 26. In the event that water were to enter the interior 40 of the storage tank 26, the water is typically drained through a sump in the base 36 of the storage tank 26, and removed from the stored petroleum.

In one example, the lower surface 24a of the floating roof 24 is configured to ride along the upper surface of the petroleum stored in the interior 40 of the storage tank 26. As a result, the floating roof 24 is configured to ride along the upper surface of the petroleum contained in the interior 40 of the storage tank 26 as the volume of petroleum contained in the interior increases and decreases. It should be appreciated that the volume of petroleum in the interior 40 of the storage tank 26 can cause the floating roof 24 to be positioned at a location such that the upper surface 24b of the floating roof 24 is disposed below an upper end of the at least one side wall 38. Accordingly, the upper surface 24b of the floating roof 24 and the inner surface 38a of the side wall 38 at an upper portion 39 of the side wall 28 that is disposed above the floating roof 24 can define a basin 42 that can be configured to collect the fluid 22, which can be provided as storm water during periods of rain.

In order to allow for the discharge of the fluid 22 from the basin 42, the storage tank 26 can include a drain 44 that extends through the floating roof 24 from the upper surface 24b to the lower surface 24a. The inlet conduit 30 can extend from the floating roof 24, and in particular from the drain 44, through the interior 40 of the petroleum storage tank 26, and out the petroleum storage tank 26 to the inlet 29 of the fluid flow separation chamber 28. Thus, the inlet conduit 30 places the drain 44 in fluid communication with the fluid flow separation chamber 28. The inlet conduit 30 can have any dimension as desired, such as a cross-sectional dimension between one inch and ten inches. The inlet conduit 30 can include a butterfly valve or any suitable alternative actuated valve as desired configured to regulate the flow of the fluid 22 through the inlet conduit. The inlet conduit 30 includes a first conduit segment 30a that extends from the drain 44 in the floating roof 24. In particular, the first conduit segment 30a can be coupled to the lower surface 24a of the floating roof 24 inside the interior 40 of the petroleum storage tank 26, and in fluid communication with the drain 44. The first conduit segment 30a can, for instance be coupled to the lower surface 24a of the floating roof 24 via a flexible or otherwise movable joint 46.

The inlet conduit 30 can further include a second inlet conduit segment 30b that extends between the first inlet conduit segment 30a and the inlet 29 of the fluid flow separation chamber 28. The second inlet conduit segment 30b can be movably coupled with respect to the first inlet conduit segment 30a. In one example, the second conduit segment 30b can attach at a first end to the inlet 29 of the fluid flow separation chamber 28. Further, the second conduit segment 30b can attach at a second end, opposite the first end, to the first conduit segment 30a. In another example, the inlet conduit 30 can include at least one intermediate conduit segment 30' coupled from the second end of the second conduit segment 30b to the first conduit segment 30a. The conduit segments can be attached to each other via a flexible or otherwise movable joint 46 as described above. Further, the first end of the second conduit segment 30b can be attached to the inlet 29 of the fluid flow separation chamber 28 via the movable joint 46. Alternatively, because the orientation of the second conduit 30b can remain constant as the floating roof 24 is raised and lowered with respect to the at least one side wall 38 due to the inclusion of the at least one intermediate conduit segment, the first end of the second conduit 30b can be fixedly attached to the inlet 29 of the fluid flow separation chamber 28. It should therefore be appreciated that the inlet conduit 30 can place the drain 44 in fluid communication with the inlet 29 of the fluid flow separation chamber both when the floating roof 24 is at a first vertical position with respect to the at least one side wall 38, and when the floating roof 24 is at a second vertical position with respect to the at least one side wall 38 that is different than the first position.

The conduit segments 30a, 30b, and 30' can be attached to each other via the movable joint 46. Accordingly, as the floating roof 24 rises and lowers with respect to the at least one side wall 38, the movable joint 46 allows the conduit segments to change in orientation and position with respect to the floating roof 24 without compromising the sealed interface between the first conduit segment 30' and the floating roof 24. Alternatively or additionally, one or more of the conduit segments 30a, 30b, and 30' can be flexible conduits.

Figure 5A:
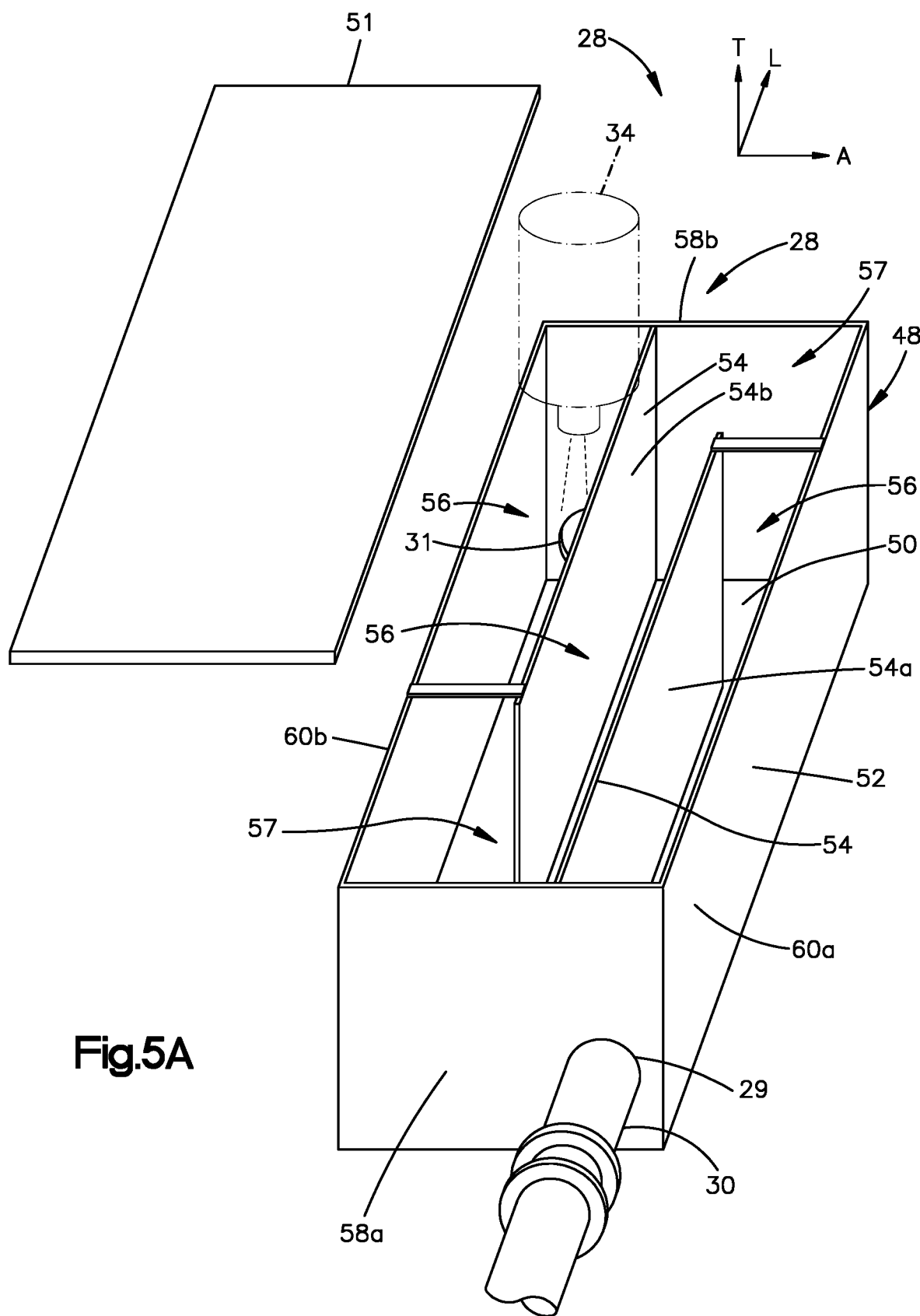
FIG. 5A is an exploded perspective view of a fluid flow separation chamber of the monitoring system illustrated in FIG. 4, constructed in accordance with one embodiment.
Figure 5B:
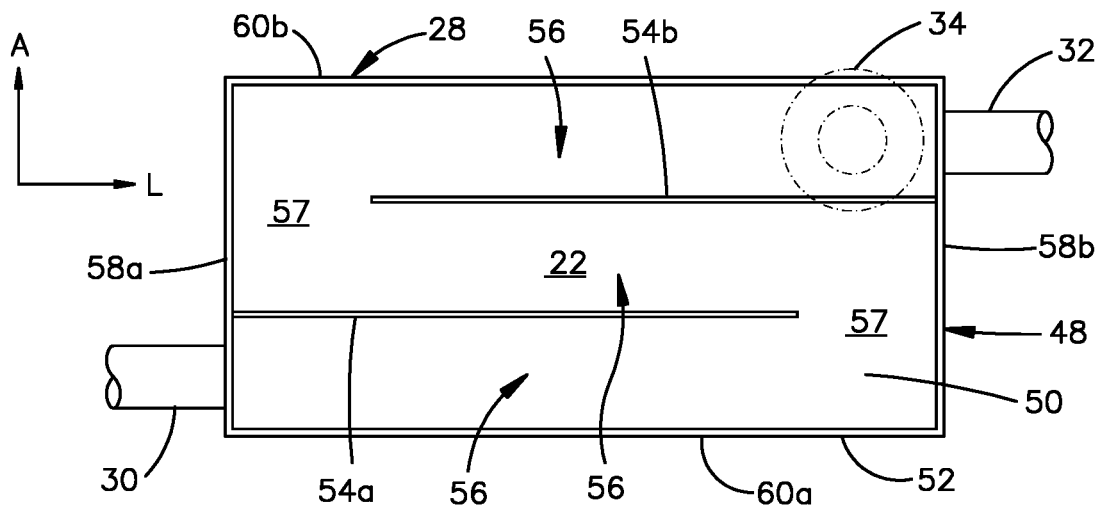
FIG. 5B is a top plan view of the fluid flow separation chamber illustrated in FIG. 5A.

Referring now also to FIGS. 5A-5B, the fluid flow separation chamber 28 defines a chamber body 48, such that the inlet 29 and the outlet 31 extend through the chamber body 48. The outlet 31 is positioned downstream from the inlet 29 with respect to the direction of the flow of fluid 22 through the chamber 28. The chamber body 48 can include a base 50 and at least one outer wall 52 that extends up from the base 50. For instance, the outer wall 52 can extend up from the base 50 along a transverse direction T. The transverse direction T can be oriented in a vertical direction during use. The base 50 and the outer wall 52 each defines a respective inner surface that cooperate with each other to define an interior 54 of the fluid flow separation chamber 28. The fluid flow separation chamber 28 can further include a heater that is configured to deliver heat to the chamber body 48, for instance the base 50, so as to prevent fluid 22 disposed in the interior 54 of the separation chamber 28 from freezing.

The chamber body 48, and thus the fluid flow separation chamber 28, further includes a plurality of baffles 54 that extend up from the base 50. For instance, the baffles 54 can extend up from the base 50 along the transverse direction T. The baffles 54 can be disposed adjacent each other along a lateral direction A that is perpendicular to the transverse direction T. The lateral direction A can thus be oriented in a horizontal direction during use. The chamber body 48, including the base 50, the baffles 54, and the outer wall 52, can be made of any suitable material as desired. In one example, the chamber body 48 can be metallic. The fluid flow separation chamber 28 defines a plurality of fluid flow channels 56 that are configured to deliver the fluid from the inlet 29 to the outlet 31. The fluid flow channels 56 can be defined between adjacent ones of the baffles 54. The fluid flow channels 56 can further be defined between outermost ones of the baffles 54 and the at least one outer wall 52. The fluid flow channels 56 can be sequentially arranged with respect to the direction of fluid flow from the inlet 29 to the outlet 31 of the fluid flow separation chamber 28. Thus, the fluid 22 travels from the floating roof 24, through the inlet conduit 30 and the inlet 29, through the fluid flow channels 56, and out the outlet 31. The baffles 54 and corresponding channels 56 direct the fluid 22 to flow in different directions sequentially at least once as it flows from the inlet 29 to the outlet 31. For instance, the different directions can be opposite directions. The separation chamber 28 can further include an upper wall 51 that is supported by the upper end of the outer wall 52, and can cover the outer wall 52 and the baffles 54. Further, the upper wall 51 can seal against the outer wall 52 and the baffles 54, thereby closing the upper ends of the fluid flow channels 56. The upper wall 51 can be configured as a cover that can be removable (for removed instance in its entirety or hinged to the chamber body 48) from the upper ends of the outer wall 52 and the baffles 54, and subsequently reattached to the chamber body 48.

In one example, each of the plurality of baffles 54 defines a first end and a second end opposite the first end with respect to a longitudinal direction L that is perpendicular to each of the transverse direction T and the lateral direction A. The longitudinal direction L can be oriented along a horizontal direction during use. The first ends of the baffles 54 can extend from the outer wall 52, and the second ends of each of the baffles 54 can be spaced from the outer wall 52. Therefore, the fluid flow separation chamber 28 defines a plurality of gaps 57 that allow the fluid 22 to flow from a respective one of the fluid flow channels 56 sequentially into an adjacent one of the fluid flow channels 56 until the fluid 22 flows out the outlet 31.

In one example, the gaps 57 can be defined by each of the baffles 54 and the outer wall 52. Thus, the gaps 57 can be at least partially defined by the baffles 54, and in particular by the second ends of the baffles 54. It should be appreciated that the gaps 57 can be defined in any suitable alternative manner as desired. For instance the baffles 54 can define openings therethrough that define the respective gaps 57 suitable to allow the fluid 22 to flow from the fluid flow channels 56 into an adjacent one of the fluid flow channels 56. The gaps 57 can be aligned with each other along a plane that can be defined by the lateral direction A and the longitudinal direction L. Further, the plane can extend parallel to the base 50. Accordingly, the fluid 22 can flow along a flow path from the inlet 29 to the outlet 31 that is defined by the longitudinal direction L and the lateral direction A. The flow path is thus defined between the base 50 and the upper wall 51. It should be appreciated that the plane can be oriented normal to the transverse direction T, as the fluid 22 flows from each of the fluid flow channels 56 into an adjacent one of the fluid flow channels 56 from the inlet 29 to the outlet 31.

The plurality of baffles 54 can include a first group of at least one baffle 54a and a second group of at least one baffle 54b that are alternatingly arranged with each other. In one example, adjacent ones of the baffles 54 can be spaced from each other along the lateral direction A. Thus, the at least one baffle 54 of the first group of at least one baffle 54a can be alternatingly arranged with the at least one baffle 54 of the second group of the at least one baffle 54b. Further, the first ends of the first group of at least one baffle 54a can be disposed opposite the first ends of the second group of the at least one baffle 54b, for instance with respect to the longitudinal direction L. The second ends of the first group of at least one baffle 54a can be disposed opposite the second ends of the second group of the at least one baffle 54b, for instance with respect to the longitudinal direction L. Thus, adjacent ones of the gaps 57 that are adjacent each other with respect to the direction of the flow of the fluid 22 through the separation chamber 28 are spaced from each other along the longitudinal direction L, and are further offset from each other with respect to the lateral direction. Thus, the baffles 54 can be oriented along respective planes that are defined by the transverse direction T and the longitudinal direction L. Accordingly, at least a pair of the baffles 54 can be oriented parallel to each other. For instance, all of the baffles can be oriented parallel to each other.

The at least one first end of the first group of at least one baffle 54a can extend from a first end of the outer wall 52. The at least one gap 57 defined by the first group of at least one baffle 54a can be disposed proximate a second end of the outer wall 52 that is opposite the first end of the outer wall 52, for instance with respect to the longitudinal direction L. Thus, the at least one gap 57 defined by the first group of at least one baffle 54a can be disposed closer to the second end of the outer wall 52 than the first end of the outer wall 52. The at least one first end of the second group of at least one baffle 54b can extend from the second end of the outer wall 52. Thus, the at least one gap 57 defined by the second group of at least one baffle 54b can be disposed proximate the first end of the outer wall 52. Thus, the at least one gap 57 defined by the second group of at least one baffle 54b can be disposed closer to the second end of the outer wall 52 than the first end of the outer wall 52. It should be appreciated that the gaps 57 defined by the first and second groups of at least one baffle 54a and 54b can define a horizontally oriented serpentine flow path for the fluid 22 traveling from the inlet 29 to the outlet 31.

The first group of at least one baffle 54a can extend from their respective first ends to their respective second ends in a first direction. The first direction can be oriented along the longitudinal direction L. The first end of each of the first group of the at least one baffle 54a extends from the outer wall 52. For instance, the first end of each of the first group of the at least one baffle 54a extends from the first end of the outer wall 52. The second end of the first group of at least one baffle 54a can define the gap 57 as described above. For instance, the first end of each of the second group of the at least one baffle 54b extends from the second end of the outer wall 52. Thus, in one example, the second end of the first group of at least one baffle 54a can be spaced from the outer wall 52. Each of the second group of at least one baffle 54b can extend from its respective first end to its respective second end along a second direction that is angularly offset from the first direction. For instance, the second direction can be opposite the first direction. Thus, the second direction can be oriented along the longitudinal direction L. The first end of each of the second group of at least one baffle 54b extends from the outer wall. The second end of each of the second group of at least one baffle 54b can define a respective gap 57 as described above. Thus, in one example, the second end of each of the second group of at least one baffle 54b can be spaced from the outer wall 52.

The outer wall 52 can define any suitable size and shape as desired. For instance, the outer wall 52 can be cylindrical, otherwise round, angled, or a combination of the above. In one example, the outer wall 52 can be rectangular in a plane that is defined by the longitudinal direction L and the lateral direction T between the base 50 and the upper wall 51. For instance, the outer wall 52 can include a first end wall 58a and a second end wall 58b opposite the first end wall 58a. For instance, the first and second end walls 58a and 58b can be opposite each other along the longitudinal direction L. The first end second ends walls 58a and 58b can extend up from the base 50. For instance, the first end second ends walls 58a and 58b can extend up from the base 50 along the transverse direction T. The first end of the outer wall 52 can be defined by the first end wall 58a, and the second end of the outer wall 52 can be defined by the second end wall 58b.

The outer wall 52 can further include a first side wall 60a and a second side wall 60b opposite the first side wall 60a. For instance, the first and second side walls 60a and 60b can be spaced from each other along the lateral direction A. Each of the first and second side walls 60a and 60b can be connected between the first and second end walls 58a and 58b. For instance, the first and second side walls 60a and 60b can each extend from the first end wall 58a to the second end wall 58b. In one example, as described above, the at least one first end of each of the first group of at least one baffle 54a extend from the first end wall 58a. The at least one second end of each of the first group of at least one baffle 54b can be spaced from the second end wall so as to define the respective at least one gap 57. The first end of each of the second group of at least one baffle 54b extend from the second end wall 58b. The second end of each of the second group of at least one baffle 54b can be spaced from the first end wall so as to define the respective gaps 57. In one example, the base 40, the outer wall 52, and the baffles 54 can define one single monolithic component. Alternatively, any one or more up to all of the base 40, the outer wall 52, and the baffles 54 can be attached to any one or more of the base 40, the outer wall 52, and the baffles 54 in any manner as desired.

The first side wall 60a can cooperate with a first laterally outermost one of the baffles 54 so as to define a respective first one of the fluid flow channels 56. The first one of the fluid flow channels 56 can be an upstream-most one of the fluid flow channels 56 with respect to the flow of the fluid 22 through the separation chamber 28. Similarly, the second side wall 60b can cooperate with a second laterally outermost one of the baffles 54 so as to define a respective second one of the fluid flow channels 56. The second one of the fluid flow channels 56 can be a downstream-most one of the fluid flow channels 56 with respect to the flow of the fluid 22 through the separation chamber 28. The fluid flow channels 56 defined between the upstream-most one of the fluid flow channels 56 and the downstream-most one of the fluid flow channels 56 can be referred to as inner fluid flow channels 56. It should be appreciated that the terms "upstream" and "downstream" and derivatives thereof are used herein with respect to the direction that the fluid 22 travels from the floating roof 24 to the second end of the outlet conduit 32, and thus from the inlet 29 to the outlet 31 of the fluid flow separation chamber 28.

The fluid flow channels 56 between the baffles can have a constant width throughout the separation chamber 28. Alternatively, the fluid flow channels 56 can have different widths. For instance, one or more channels 56 disposed downstream of one or more upstream channels 56 can have a respective width greater than that of the upstream channels 56. The width can be measured along a lateral direction A between adjacent ones of the baffles 54, or with respect to outermost channels 56 between the outermost ones of the baffles 54 and the outer wall 52. Thus, it should be appreciated that the fluid flow channels 56 can define a constant cross-sectional area. Alternatively, one or more of the channels can have a greater cross-sectional area than one or more others of the fluid flow channels 56. For instance, the one or more channels having the greater cross-sectional area can be disposed downstream of the one or more others of the fluid flow channels 56. The cross-sectional area of the fluid flow channels 56 can, for instance, be measured along a plane that is oriented along a direction normal to the direction of fluid flow through the fluid flow channels 56. In one example, the plane can be defined by the transverse direction T and the lateral direction A.

During operation, the fluid 22 enters the inlet 29 of the fluid flow separation chamber 28. The fluid 22 then travels sequentially through the upstream-most one of the fluid flow channels 56, the inner fluid flow channels, and the downstream-most one of the fluid flow channels 56 along a serpentine flow path between the inlet 29 and the outlet 31. For instance, the fluid 22 can travel alternatingly in the first direction through respective first ones of the fluid flow channels 56, and in the second direction through respective second ones of the fluid flow channels 56. The first and second directions can be oriented substantially along the longitudinal direction L, taking into account variations in the fluid flow through the fluid flow channels 56. The fluid 22 can travel along the lateral direction A through the gaps 57 between the adjacent fluid flow channels 56. The fluid 22 then exits the fluid flow separation chamber 28 out the outlet 31. The fluid flow separation chamber 28 is configured to cause the fluid 22 to flow through the fluid flow channels 56 at a flow rate that is less than the flow rate through the inlet conduit 30. For instance, adjacent ones of the baffles 54 can be spaced a first distance along the lateral direction A, and the inlet 29 defines a cross-sectional direction along the lateral direction A, such that the first distance is greater than the cross-sectional dimension. Further, the outlet 31 can define a cross-sectional area that is substantially equal to the cross-sectional area of the inlet 29. Alternatively or additionally, the height of the baffles 54 from the base 40 to the upper ends of the baffles 54 can be spaced a distance that is greater than the cross-sectional dimension of the inlet 29. Accordingly, a cross-sectional area of the fluid 22 along a plane defined by the transverse direction T and the lateral direction A in the fluid flow channels 56 is greater than the cross-sectional area of the fluid 22 in the inlet conduit 30.

The separation chamber 28 can cause the flow rate of the fluid 22 to decrease with respect to the flow rate of the fluid 22 through the inlet conduit 30, such that separation chamber 28 causes the flow of the fluid 22 to become laminar. As a result, hydrocarbons present in the fluid 22 will rise to the upper surface of the fluid 22 in the chamber 28 between the inlet 29 and the outlet 31. Accordingly, the hydrocarbon sensor 34 can reliably detect the hydrocarbons in the fluid 22. In one example, the hydrocarbon sensor 34 is configured to output a signal in response to a detection of the threshold amount of hydrocarbons in the fluid 22 that travels through the fluid flow separation chamber 28 along a direction from the inlet 29 to the outlet 31. The sensor 34 can be supported by the separation chamber 28 or alternative suitable structure, such that the sensor 34 is positioned to detect a threshold amount of hydrocarbons in the fluid 22 at a location adjacent the outlet 31 of the separation chamber 28. The threshold amount can be an amount sufficient to cause a sheen at the upper surface of the fluid 22. Thus, the sensor 34 can be configured to detect hydrocarbons at the upper surface of the fluid 22. For instance, the sensor 45 can be positioned such that it detects hydrocarbons at the upper surface of the fluid 22 while the fluid is in the separation chamber 28. Thus, in one example, the location adjacent the outlet 31 is inside the fluid flow separation chamber 28. It should be appreciated that the sensor 34 can be configured to detect petroleum at any suitable location of the separation chamber 28 where it is expected that the hydrocarbons will be present at the upper surface of the fluid 22. The sensor 34 can be mounted to the chamber body 48, such as the outer wall 52. It should be appreciated, of course, that the hydrocarbon sensor 34 can be mounted to any suitable alternative structure such that the sensor 34 is in operable communication with the fluid 22 so as to sense the threshold amount of petroleum in the fluid 22. For instance, it is envisioned that in certain examples the sensor can be positioned so as to detect the presence of hydrocarbons in the fluid 22 at a location downstream from the outlet 31.

As described above, and referring to FIG. 7, the hydrocarbon sensor 34 is configured to output a signal in response to a detection of the threshold amount of hydrocarbons in the fluid 22. The signal can be transmitted over a hard wire, or wirelessly as desired. The signal can be received by a processor, or the hydrocarbon sensor 34 can include a processor, that receives the signal and, in response to the signal, sends command signals to one or more peripheral devices, for instance to close a valve that halts the flow of the fluid 22 through the separation chamber 28 as described in more detail below. The command signals can be communicated over a hard wire, or wirelessly as desired. Alternatively, the peripheral devices can include a processor that receives the signal directly from the hydrocarbon sensor 34 and, in response to the signal, activates an alarm condition. For instance, the peripheral devices can include at least one audio alarm 62, at least one visual alarm 64, and at least one remote transmitter 66 configured to transmit a remote alarm. The audio alarm 62 can be disposed local to the separation chamber 28. Alternatively, the audio alarm 62 can be located remote from the separation chamber 28, for instance in a control room.

The audio alarm 62 is configured to emit an audible signal in response to the detection of the threshold amount of petroleum as sensed by the hydrocarbon sensor 34. Similarly, the visual alarm 64 can be disposed local to the separation chamber 28. Alternatively, the visual alarm 64 can be located remote from the separation chamber 28, for instance in the control room. The visual alarm 64 is configured to emit a visible alarm in response to the detection of the threshold amount of petroleum as sensed by the hydrocarbon sensor 34. The at least one remote transmitter 66 can likewise be disposed local to the separation chamber 28. Alternatively, the audio alarm 62 can be located remote from the separation chamber 28, for instance in a control room. The remote transmitter 66 can be configured to send an alarm signal to a remote location. For instance, the remote transmitter 66 can initiate and send a message, such as a text message, email, phone call, or the like, to a user indicating the alarm condition. Alternatively or additionally, the remote transmitter 66 can update a webpage or other communications medium for detection by a user. Alternatively, the system 20 can include a web-browser application that allows a remote user to monitor the status of one or more separation chambers 28 disposed at various locations, and operate the system 20 remotely as desired.

It is further recognized that diagnostic output can be sent to the remote user advising the user of the status of the sensor 34. For instance, when the sensor 34 outputs a first signal having a first value, such as a first range of millivolts, a diagnostic unit coupled to the sensor 34 can conclude that the sensor 34 is in a fault condition, and needs to be serviced. When the sensor 34 outputs a first signal having a second value different than the first value, such as a second range of millivolts, the diagnostic unit concludes that the sensor 34 is operating normally without sensing hydrocarbons. When the sensor 34 outputs a third signal having a third value different than the first and second values, such as a third range of millivolts, the diagnostic unit concludes that the sensor 34 is operating normally and has sensed the presence of hydrocarbons. The second value can be greater than the first value, and the third value can be greater than each of the first and second values.

Figure 6A:
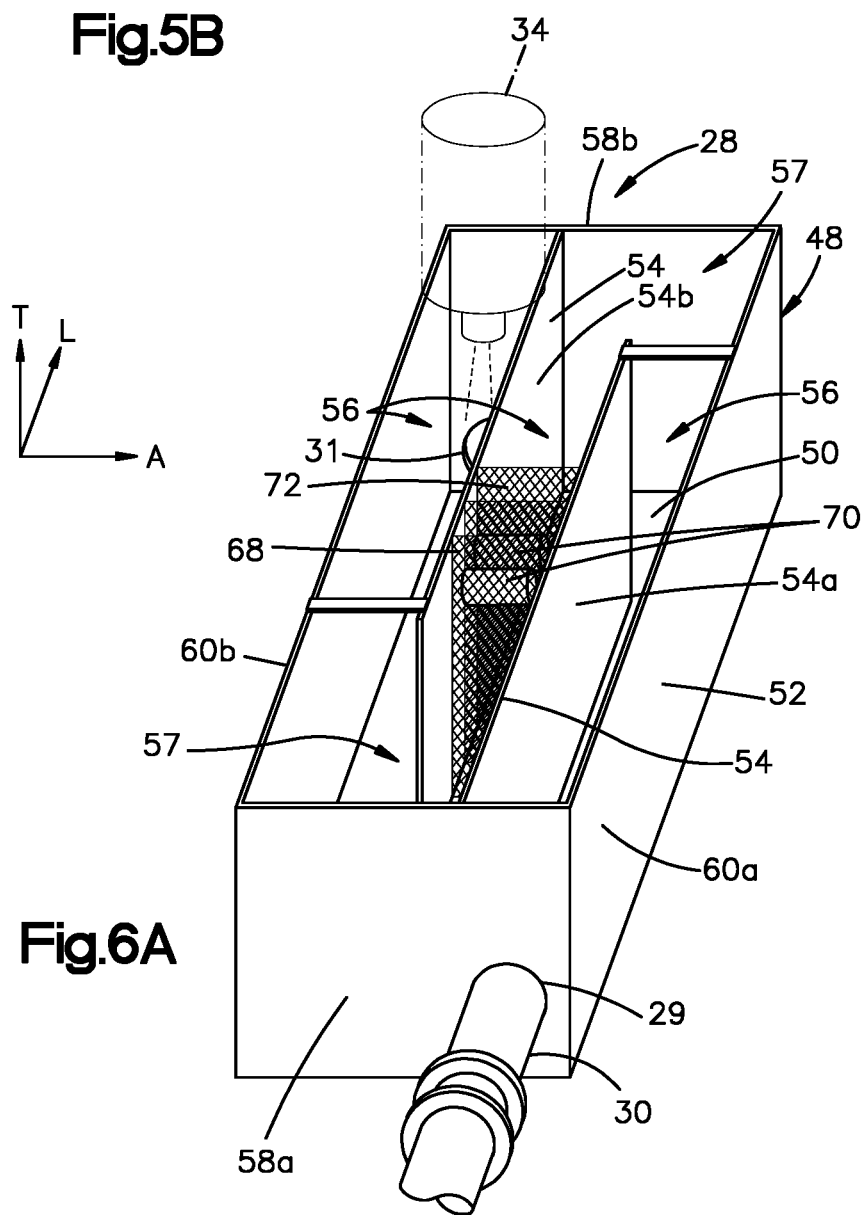
FIG. 6A is a perspective view of a fluid flow separation chamber similar to the fluid flow separation chamber illustrated in FIG. 5A, but including an absorbent member in accordance with an alternative embodiment.

Referring now to FIG. 6A, it is envisioned that in some situations during use, the petroleum storage tank 26 may allow petroleum to enter the fluid 22 at a minimal rate, such that only a trace amount of hydrocarbons are present in the fluid 22. Accordingly, the monitoring system 20 can include at least one oil-absorbent media 68 that is positioned in at least one of the fluid flow channels 56, such that at least a portion of the fluid 22 passes through the oil-absorbent media 68. If the fluid 22 passing through the oil-absorbent media 68 contains petroleum or other hydrocarbons, the oil-absorbent media 68 can absorb some up to all of the hydrocarbons in the fluid 22 prior to the fluid 22 traveling past the sensor 34. Accordingly, hydrocarbons that may have been present in the fluid 22 in a sufficient quantity to cause the sensor 34 to detect an alarm condition can be absorbed by the media 68 in sufficient quantity that allows the fluid 22 to flow past the sensor 22 without detection of hydrocarbons in sufficient quantity that causes the alarm condition.

In one example, the separation chamber 28 can include at least one or more absorptive members 70 that comprises the absorptive media 68. In particular, the oil-absorbent media can be supported in at least one of the fluid flow channels 56. For instance, the oil-absorbent media 68 can be supported by at least one of the base 50, the outer wall 52, and at least one of the baffles 54. The oil-absorbent media 68 can be disposed at a location such that the oil-absorbent media 68 is positioned to remove the petroleum from the fluid 22. In one example, the oil-absorbent media 68 can be hydrophobic. For instance, the oil-absorbent media 68 be configured as any suitable material commercially available from Miller Waste Mills, Inc. having a place of business in Winona, Minn. Alternatively, the oil-absorbent media 68 can be commercially available from Phase III, Inc., having a principle place of business in Chandler, Ariz. Alternatively still, the oil-absorbent media 68 can be commercially available from Universal Remediation, Inc., having a place of business in Pittsburgh, Pa. Visual inspection of the oil-absorbent media 68 can allow a user to assess whether petroleum is being introduced into the fluid 22 even though the sensor 34 is not detecting the threshold amount of petroleum in the fluid 22 sufficient to indicate an alarm condition. Thus, the user can replace or clean the oil-absorbent media 68, and can proactively take steps to address the source of petroleum ingress into the fluid 22.

As described above, it is recognized that the separation chamber 28 can be configured to cause hydrocarbons in the fluid 22 to rise to the upper surface of the fluid 22 to create a sheen as the fluid 22 travels through the separation chamber 28. Accordingly, the oil-absorbent media 68 can be positioned such that the upper surface of the fluid 22 flowing through the separation chamber 28 is aligned with a portion of the absorptive media 68. Thus, the oil-absorbent media 68 can define at least a location that is spaced up from the base 50. For instance, the oil-absorbent media 68 can be movably supported at an upper end of the chamber body 48 in one of the fluid flow channels 56 such that the flow of the fluid 22 through the one of the fluid flow channels 56 can cause the oil-absorbent media 68 to rise to the upper surface of the fluid 22 as the fluid 22 travels past the oil-absorbent media 68. For instance, the monitoring system 20 can include at least one cage 72 that each contains at least one the oil-absorbent member 70 that is made of the oil-absorbent media 68. The oil-absorbent member 70 can be cylindrical in shape or can define any alternative suitable shape as desired. The petroleum absorbent member 70 can, for instance, be positioned so as to extend between and from adjacent ones of the baffles 54, or an outermost one of the baffles 54 and the outer wall 52. The cage 72 is fluid-permeable, such that the cage 72 allows the fluid 22 to flow therethrough between the inlet 29 and the outlet 31 of the separation chamber 28. The cage 72 can be pivotally attached to the chamber body 48 or the upper wall 51, such that the cage 72, and thus the contained oil-absorbent media 68, rides along the upper surface of the fluid 22 as the fluid 22 travels through the separation chamber 28. The separation chamber 28 can include a plurality (e.g., more than one) cage 72, disposed in series with respect to the flow of the fluid 22 through the separation chamber 28. Thus, one of the oil-absorbent members 70 can be disposed downstream of another one of the oil-absorbent members. When the absorbent members 70 have become saturated with petroleum, the saturated absorbent members 70 can be replaced with new absorbent members 70. For instance, the cage 72 can be opened, the saturated absorbent members 70 can be removed, new absorbent members 70 can be inserted into the cage 72, and the cage 72 can be closed.

Figure 6B:
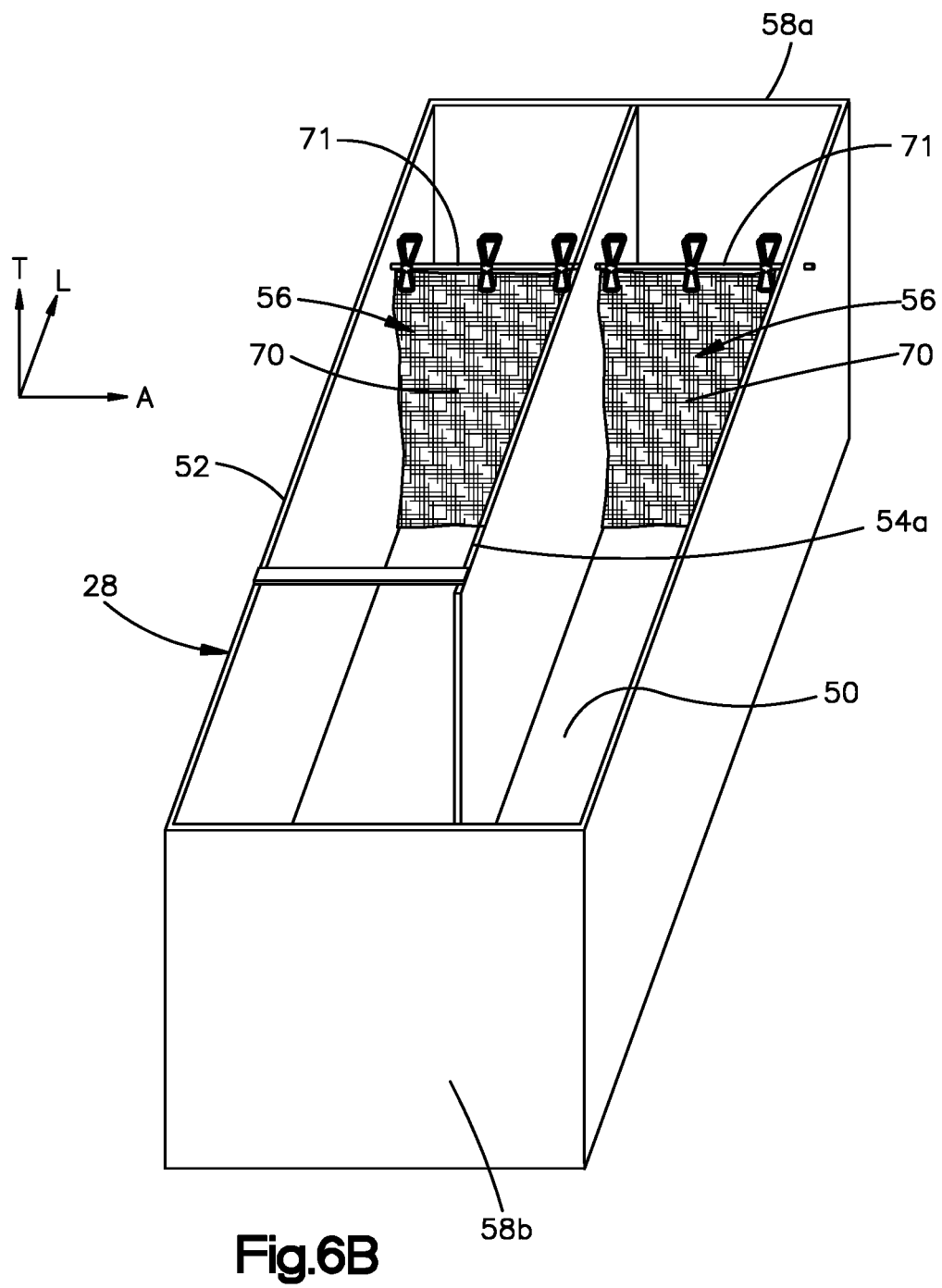
FIG. 6B is a perspective view of a fluid flow separation chamber similar to the fluid flow separation chamber illustrated in FIG. 6A, but including an absorbent member in accordance with another alternative embodiment.

Alternatively, as illustrated in FIG. 6B, which illustrates a portion of the fluid flow separation chamber 28, the petroleum absorbent member 70 can be pivotally attached to a pivot member 71 that is in turn pivotally attached to the chamber body 48. For instance, the pivot member 71 can be a rod that extends through apertures in the separation chamber walls, and thus is rotatably in the walls. The petroleum absorbent member 70 can be attached to the pivot member at its upper end, such that the petroleum absorbent member 70 is configured to ride along the upper surface of the fluid in the manner described above with respect to FIG. 6A.

Figure 8A:
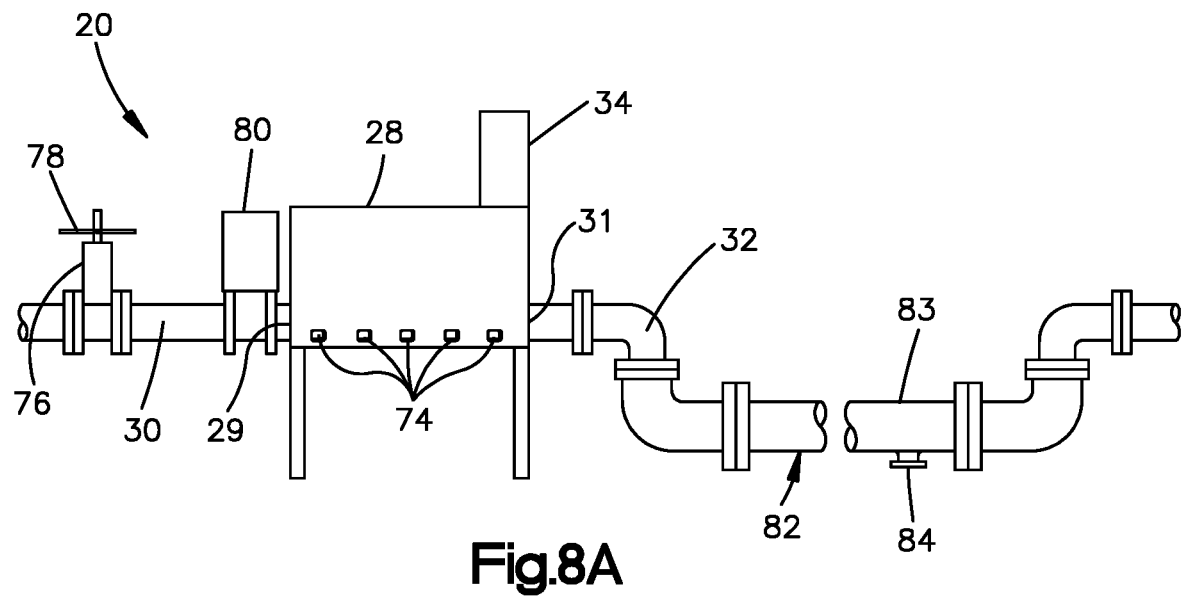
FIG. 8A is a schematic side elevation view of a monitoring system constructed in accordance with an alternative embodiment.
Figure 8B:
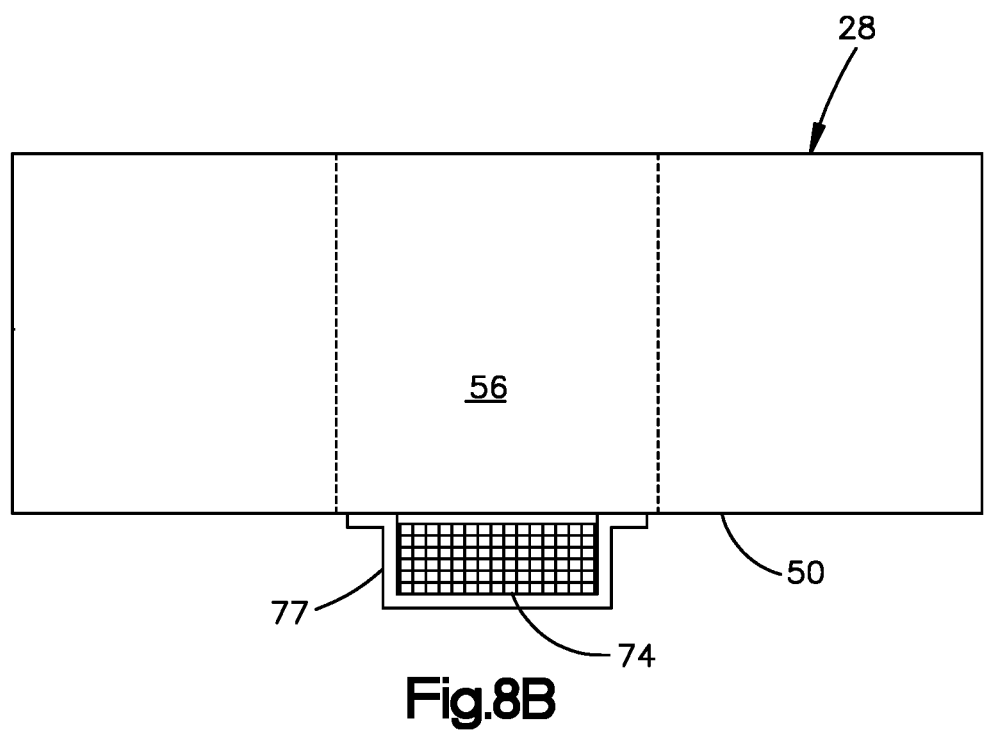
FIG. 8B is a schematic side elevation view of a fluid flow separation chamber constructed in accordance with an alternative embodiment.

Referring now to FIGS. 8A-8B, the separation chamber 28 can further include at least one magnet 74 such as a plurality of magnets 74 that are mounted to any suitable location of the chamber body 48 in at least one or more up to all of the fluid flow channels 56, such as the base 50, the outer wall 52, and one or more of the baffles 54. For example, the magnets 74 can be mounted to at least one of the inner surfaces of the base 50 and the outer wall 52. The chamber body 48 can be made of a ferrous material, such that the at least one magnet 74 is magnetically fastened to the chamber body 48. Because the at least one magnet 74 is positioned in the flow of the fluid 22, the at least one magnet 74 can attract and attach, directly or indirectly, to ferrous particulates disposed in the fluid 22.

It has been discovered that, particularly in a floating roof storage tank, as the roof 24 translates up and down, the corresponding seals bear against the inner surface of the tank 26. Continuous usage can cause the inner surface of the outer wall of the tank 26 to wear and scale, thereby generating particulates that sit atop the floating roof 24. Consequently, rainwater can direct the particulates through the drain 44 and ultimately into the separation chamber 28. As the particulates flow through the separation chamber 28, they become attached to the magnets 74, and are prevented from flowing through the outlet 31. In one example, the particulates can be rusted or otherwise corroded steel from the inner surface of the side wall of the storage tank 26. The magnetic field of the magnets 74 attracts the particulates to the magnets 74, such that the particulates attach to the magnets and are prevented from exiting the separation chamber 28 through the outlet 31.

It has been further discovered that the inlet conduit 30 can be susceptible to corrosion, particularly when used in environments with high salt concentrations in the air, for instance, near an ocean. As the inner surface of the inlet conduit 30 corrodes, particles from the inner surface of the inlet conduit 30 are produced that are visually distinguishable from the particles from the inner surface of the outer wall of the tank. For instance, the particles from the inlet conduit 30 are typically substantially larger than the particles from the outer wall of the tank. Further, while the scaling from the inner surface of the outer wall of the tank 26 can be observed through visual inspection of the outer wall of the tank 26, corrosion of the inner surface of the inlet conduit 30, on the contrary, is not easily detected by visual inspection as the inlet conduit 30 resides in the interior of the tank 26. The particles from the inlet conduit 30 travel with the fluid 22 into the separation chamber 28 where they attach to the one or more magnets 74.

Visual inspection of the particles attached to the magnet 74, for instance based on size and/or shape, can indicate to the user where the particulates originated. For instance, the size of plurality of the particles from the inlet conduit 30 are typically greater than the size of plurality of the particles of the outer wall of the tank 26. In particular, the presence of a grouping of larger particles attached to the one or more magnets 74 can indicate that structural integrity of the inlet conduit 30 is being compromised. Thus, the user can further investigate or determine that one or more segments of the inlet conduit 30 should be repaired or replaced. Accordingly, a method can include the steps of generating the particles from the outer wall of the tank and the inlet conduit, attaching the particles to the at least one magnet 74, and visually inspecting the particles to identify an identifying characteristic that distinguishes the particles from the outer wall of the storage tank 26 and the particles from the inlet conduit 30. The identifying characteristic can be a size.

In order to facilitate the easy removal of the particulates from the magnets 74, the magnets 74 can be disposed in a physical barrier, such as a film. It is desirable for the physical barrier to be usable in the fluid 22 that is received in the separation chamber 28. In one example, each of the magnets can be disposed in its own barrier. Alternatively, more than up of the magnets 74 can be disposed in a common barrier. The film can be porous with respect to magnetic field, such that the magnetic field of the magnets 74 travels through the film and causes the particles in the fluid 22 to attach to the magnets 74. To remove the particulates from the magnets 74, the magnets 74 can be removed from the barrier. The barrier can then be cleaned and reused. Alternatively, the barrier can be disposable and discarded, and a new barrier can be placed about the magnet 74. It can be said that the particulates attach to the magnets whether or not the magnets are disposed in the barrier. The barrier can, for instance, be made of any film material, such as rubber, for instance nitrile, neoprene, or latex. The film can define an interior within which the magnets 74 are disposed. Alternatively, the film can be wrapped around the magnets 74.

In another example illustrated in FIG. 8B, the at least one magnet 74 can be mounted onto an exterior surface of the fluid flow separation chamber 28 that is opposite the interior 54. The at least one magnet 74 can be operatively aligned with a respective at least one of the fluid flow channels 56, such that the at least one magnet 74 directs a magnetic force into the at least one of the fluid flow channels 56 sufficient to entrap ferrous particulates that are traveling with the fluid through the separation chamber 28. In one example, the at least one magnet 74 can be disposed beneath the base 50, such that the base 50 is disposed between the interior 54 of the fluid flow separation chamber 28 and the magnets 74. The at least one magnet 74 can include a plurality of magnets that are each aligned with a respective one or more up to all of the fluid flow channels. As ferrous particulates disposed in the fluid travels through the fluid flow separation chamber 38, they become attached to the base 50 at a location of the base 50 that is operably aligned with the magnets 74. Thus, the magnets 74 are configured to entrap the ferrous particulates, either through direct attachment (for instance when the magnets 74 are disposed in the interior 54 of the separation chamber) or through indirect entrapment (for instance, when the magnets 74 are disposed in a barrier or are mounted to the exterior of the separation chamber 28). The magnets 74 can be housed in any suitable containment apparatus 77 such as a drawer. The drawer can be moved between a closed position whereby the magnets are operatively aligned with the fluid flow channels 56, and an open position that allows the magnets 74 to be removed. Thus, when the fluid flow separation chamber 28 is disconnected from incoming fluid, the magnets 74 can be removed from the separation chamber 28, and the base 50 can be cleaned of accumulated ferrous particulates.

Referring now to FIG. 8A, the monitoring system 20 can include one or more valves that are configured to move between an open position and a closed position. When in the open position, the valves permit the fluid 22 to flow therethrough, and when in the closed position, the valves prevent the fluid 22 from flowing therethrough. For instance, the monitoring system 20 can include a manual valve 76 disposed upstream of the separation chamber 28 with respect to the direction of the fluid flow. For instance, the manual valve 76 can be disposed in the inlet conduit 30 at a location between the petroleum storage tank 26 and the inlet 29 of the separation chamber 28. The manual valve 76 can include a manual actuator 78 that can be moved between a first position that places the manual valve 76 in the open position, and a second position that places the manual valve 76 in the closed position. When the manual valve 76 is in the open position, the manual valve 76 does not prevent the flow of the fluid 22 from the petroleum storage tank 26 to the separation chamber 28. When the manual valve 76 is in the closed position, the manual valve 76 prevents the fluid from flowing from the petroleum storage tank 26 to the separation chamber 28. Thus, the manual valve 76 is configured to prevent the fluid 22 from flowing from the petroleum storage tank 26 to the separation chamber 28 even when the hydrocarbon sensor 34 does not detect an alarm condition.

The monitoring system 20 can further include at least one automatic valve that is configured to move between the open position and the closed position depending on the sensed condition of the hydrocarbon sensor 34. In particular, as described above, the hydrocarbon sensor 34 is configured to output a signal in response to a detection of the threshold amount of hydrocarbons in the fluid 22. The signal can be received by a processor, or the hydrocarbon sensor 34 can include a processor, that receives the signal and, in response to the signal, send command signals to one or more peripheral devices. Alternatively, the peripheral devices can include a processor that receives the signal directly from the hydrocarbon sensor 34 and, in response to the signal, activates an alarm condition. The peripheral devices can include the at least one automatic valve. The at least one automatic valve can be in the open position when the hydrocarbon sensor 34 does not detect the threshold amount of hydrocarbons in the fluid 22. When the hydrocarbon sensor 34 outputs the signal in response to a detection of the threshold amount of hydrocarbons in the fluid 22, the at least one automatic valve in response moves from the open position to the closed position. When the hydrocarbon sensor 34 does not detect the threshold amount of hydrocarbons in the fluid 22, the at least one automatic valve can operate in the open position. Thus, the at least one automatic valve can be referred to as a normally open valve.

The at least one automatic valve can include an automatic inlet valve 80 that can be disposed in the inlet conduit 30. The inlet valve 80 can be disposed between the inlet 29 of the separation chamber 28 and the manual valve 76. Alternatively, the manual valve 76 can be disposed between the automatic inlet valve 80 and the inlet 29 of the separation chamber 28. It should be appreciated that the second end of the inlet conduit 30 can be defined by either the manual valve 76 or the inlet valve 80. Alternatively, both the manual valve 76 and the inlet valve 80 can be disposed between the first and second ends of the inlet conduit 30. During operation, when the hydrocarbon sensor 34 does not detect the threshold amount of hydrocarbons in the fluid 22, the automatic inlet valve 80 does not prevent the fluid 22 from flowing from the floating roof 24 to the separation chamber 28. Accordingly, when both the manual valve 76 and the automatic inlet valve 80 are in the open position, the fluid 22 is able to flow from the floating roof 24 through the inlet conduit 30 and into the separation chamber 28. When either of the manual valve 76 and the automatic inlet valve 80 is in the closed position, the fluid 22 upstream of the closed one of the manual valve 76 and the automatic inlet valve 80 is prevented from flowing to the separation chamber 28. The fluid 22 upstream of the closed one of the manual valve 76 includes the fluid 22 disposed on the floating roof 24 and in the inlet conduit 30 at a location of the inlet conduit 30 that is upstream of the closed one of the manual valve and the automatic inlet valve 80.

It is recognized that when the threshold amount of hydrocarbons is present in the fluid 22 and the automatic inlet valve 80 is therefore moved to the closed position, the fluid 22 in the separation chamber 28 may contain hydrocarbons in a quantity such that it is undesirable to deliver the fluid 22 into the environment. Accordingly, the outlet conduit 32 can include a region 82 that is sized and configured to retain the fluid 22 disposed in the separation chamber 28 after one or both of the manual valve 76 and the automatic inlet valve 80 has been moved to the closed position. In particular, the region 82 can define a P-trap 83. For instance, the region 82 can extend down and then up so as to define a substantial U-shape. The volume of the region 82 of the outlet conduit 32 can be at least equal to the volume of the separation chamber 28. For instance, the volume of the region 82 of the outlet conduit can be at least equal to the volume of the separation chamber 28 in addition to the length of the inlet conduit 30 that is disposed downstream of one or both of the valves 76 and 80. Accordingly, once the threshold amount of hydrocarbons is sensed in the fluid 22, the fluid 22 that is disposed upstream from the sensed fluid is prevented from flowing into the ambient environment. Further, the outlet conduit 32 can define a drain 84 in the region 82 that can be opened so as to direct the fluid 22 disposed in the region through a drainage tube and into any suitable containment apparatus where the fluid 22 can be analyzed, and the hydrocarbons can be removed prior to delivering the fluid 22 to the ambient environment. Thus, the hydrocarbon laden fluid 22 in the separation chamber 28 can be safely removed without delivering the hydrocarbon into the ambient environment.

Figure 9:
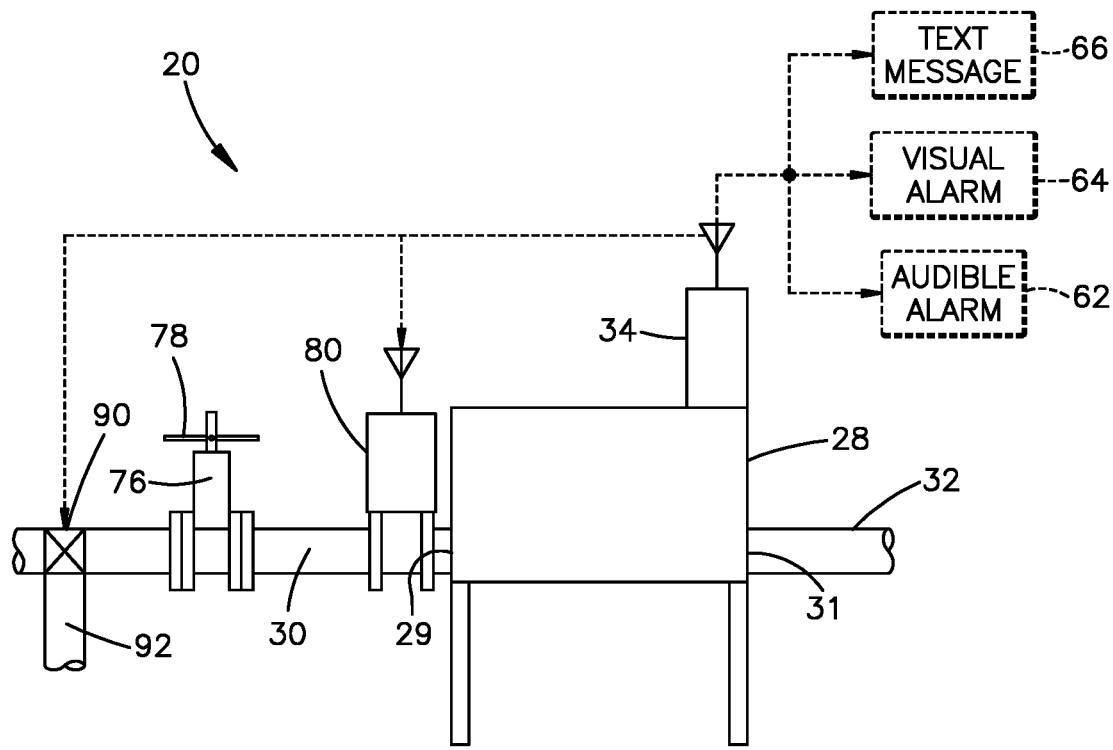
FIG. 9 is a schematic side elevation view of a monitoring system constructed in accordance with yet another alternative embodiment.
Figure 10:
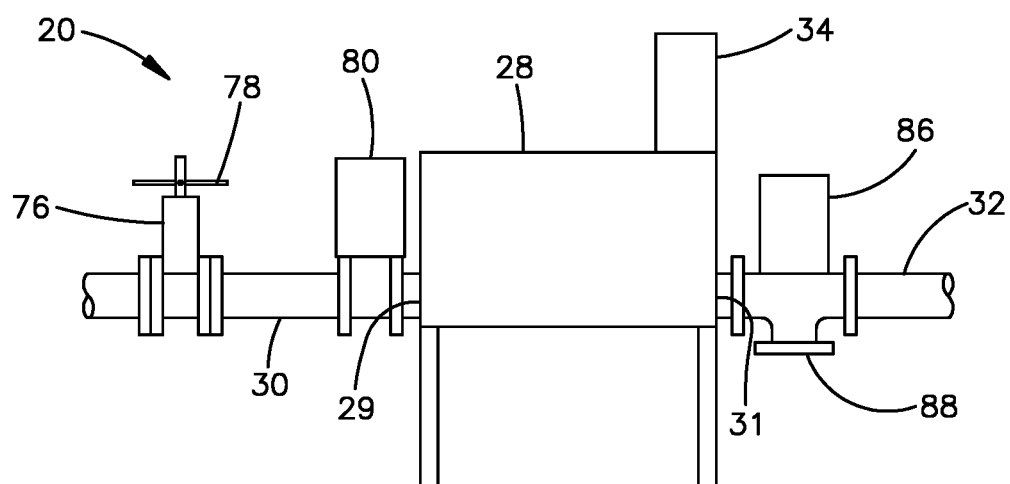
FIG. 10 is a schematic side elevation view of a monitoring system constructed in accordance with still another alternative embodiment.

Alternatively or additionally, referring now to FIGS. 9-10, the at least one automatic valve can include an automatic outlet valve 86 that can be disposed in the outlet conduit 32. The first end of the outlet conduit 32 can be defined by the outlet valve 86. Alternatively, the outlet valve 86 can be disposed between the first and second ends of the outlet conduit 32. During operation, when the hydrocarbon sensor 34 does not detect the threshold amount of hydrocarbon in the fluid 22, the automatic outlet valve 86 is in the open position, and thus does not prevent the fluid 22 from flowing from the separation chamber 28 out the second end of the outlet conduit 32 and into the ambient environment. When the hydrocarbon sensor 34 detects the predetermined threshold amount in the fluid 22, the automatic outlet valve 86 moves to the closed position in response to the signal, and thus prevents the fluid 22 disposed in the separation chamber 28 from flowing through the outlet conduit 32 and into the ambient environment.

Further, referring now to FIG. 10, the monitoring system 20 can further include an outlet drain 88 that is configured to drain the fluid captured between the closed outlet valve 86 and the closed manual valve 76 or automatic inlet valve 80. The outlet drain 88 can be disposed between the outlet valve 86 and the downstream-most one of the manual valve 76 and the automatic inlet valve 80. In one example, the outlet drain 88 can be disposed between the outlet 31 of the separation chamber 28 and the outlet valve 86. Alternatively, the outlet drain 88 can be defined by the outlet valve 86. The outlet drain 88 is configured to be opened after the outlet valve 86 has been closed, so as to direct the fluid 22 disposed between the inlet valve 80 and the outlet valve 86 into any suitable containment apparatus where the fluid 22 can be analyzed, and the hydrocarbons can be removed prior to delivering the fluid 22 to the ambient environment. Thus, the hydrocarbon laden fluid 22 in the separation chamber 28 can be safely removed without delivering the hydrocarbon into the ambient environment. The base 50 can be sloped downward along a direction from the inlet 29 toward the outlet drain 88, so as to assist in directing the flow of fluid 22 from the inlet 29 toward the outlet drain 88. In one example, the automatic outlet valve 86 can prevent fluid from flowing from the outlet 31 to the outlet conduit 32.

It is appreciated that it is desirable to ensure that once the valve or vales are closed in response to the sensed threshold amount of hydrocarbons, the closed valve or valves do not reopen while petroleum remains present. Accordingly, in one example, it can be desirable to ensure that a quantity of fluid 22 is disposed in the separation chamber 28. So long as fluid 22 is disposed within the chamber, the sensor will detect the presence of the threshold amount of hydrocarbons when present. If, on the other hand, fluid 22 is entirely removed from the separation chamber 28, the sensor 22 would not detect hydrocarbons, and thus would cause the inlet and outlet valves to open, even though a condition exists that is allowing hydrocarbons to enter the fluid 22. Accordingly, it may be desirable to space the outlet drain 88 above the base of the separation chamber 28. Alternatively, the region 82 of the outlet conduit 32 can be located slightly above the outlet 88 of the separation chamber 28. Alternatively still, the fluid 22 can be removed in its entirety from the separation chamber 28, and the monitoring system 20 can operate such that the closed valve or valves are not allowed to open until a user causes them to open. As a result, the system will not allow hydrocarbon-laden fluid to enter and potentially exit the separation chamber 28 unless a user manually inspects the monitoring system 20.

Referring again to FIG. 9, it is recognized that when the threshold amount of hydrocarbons is sensed in the fluid 22 and the automatic inlet valve 80 is moved to the closed position, a substantial volume of fluid 22 may remain on the floating roof 24, and the volume of fluid 22 can continue to accumulate during periods of rain. Accordingly, in order to remove the fluid 22 from the petroleum storage tank 26 after the threshold amount of hydrocarbons is sensed in the fluid 22, the monitoring system 20 can include a bypass valve 90 in the inlet conduit 30, and a bypass conduit 92 that extends from the inlet conduit 30. The bypass valve 90 can be moved between an open position and a closed position. When the bypass valve 90 is in the closed position, the bypass valve 90 prevents the fluid 22 from flowing from the inlet conduit 30 to the bypass conduit 92. When the bypass valve 90 is in the open position, the bypass valve 90 allows the fluid 22 to flow from the inlet conduit 30 to the bypass conduit 92. In one example, when the bypass valve 90 is in the open position, the bypass valve can cause the fluid 22 to flow from the inlet conduit to the bypass conduit 92. The bypass conduit 92 can direct the fluid 22 into any suitable containment apparatus that allows the fluid 22 to drain from the floating roof 24 of the storage tank.

The bypass valve 90 can be disposed upstream of the automatic inlet valve 80. The bypass valve 90 can further be positioned upstream of the manual valve 76. Similarly, the bypass conduit 92 can be disposed upstream of the automatic inlet valve 80. The bypass conduit 92 can further be positioned upstream of the manual valve 76. The bypass conduit 92 can extend from the inlet conduit 30 to the containment apparatus that is configured to receive the fluid 22 from the storage tank, thereby allowing the fluid 22 to drain from the floating roof 24. During operation, the bypass valve 90 is in the closed position while the hydrocarbon sensor 34 does not detect the threshold amount of hydrocarbons in the fluid at the threshold amount. When the hydrocarbon sensor 34 detects the threshold amount of hydrocarbons in the fluid 22, the bypass valve 90 can be moved from the closed position to the open position. For instance, the bypass valve 90 can be moved from the closed position to the open position by a user. Alternatively, the bypass valve 90 can be manually moved from the closed position to the open position upon generation of the signal from the hydrocarbon sensor 34 that the threshold amount of hydrocarbons has been detected in the fluid 22. Thus, the bypass valve 90 can be included in the peripheral devices that are configured to automatically actuate in response to the detection of the threshold amount of hydrocarbons in the fluid 22. Because the inlet valve 80 is in the closed position when the threshold amount of hydrocarbons has been detected in the fluid 22, the fluid 22 disposed upstream of the bypass valve 90 flows through the bypass conduit 92. The fluid 22 can be analyzed at the containment apparatus, and any hydrocarbons disposed in the fluid 22 can be removed from the fluid 22, such that the fluid 22 can then be released into the ambient environment.

Figure 11A:
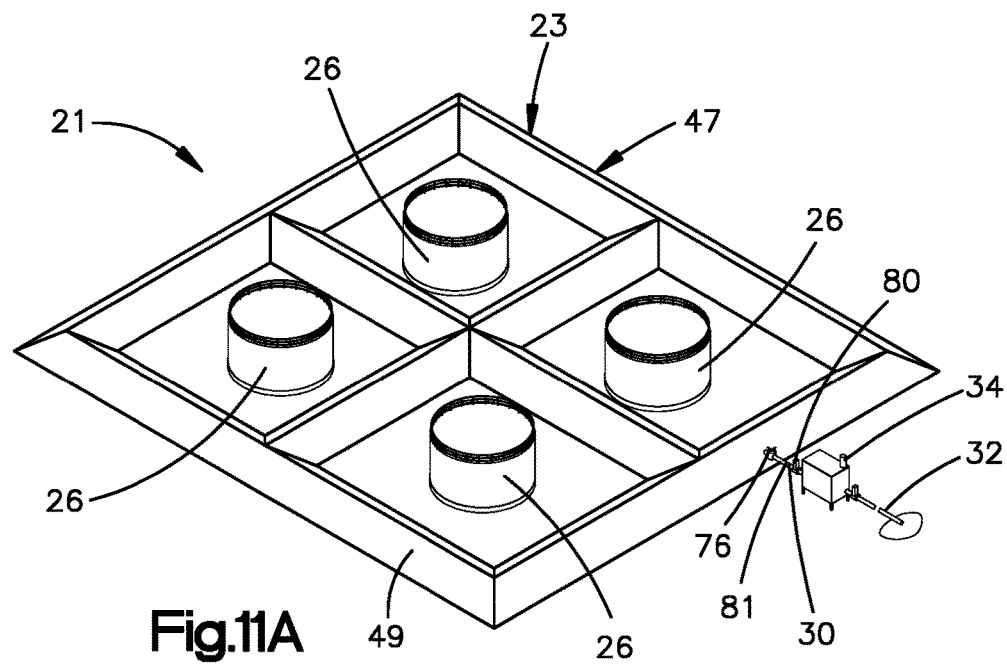
FIG. 11A is a schematic perspective view of a petroleum storage facility including a containment area and a run off retention pond, showing the monitoring system operatively coupled to the containment area.
Figure 11B:
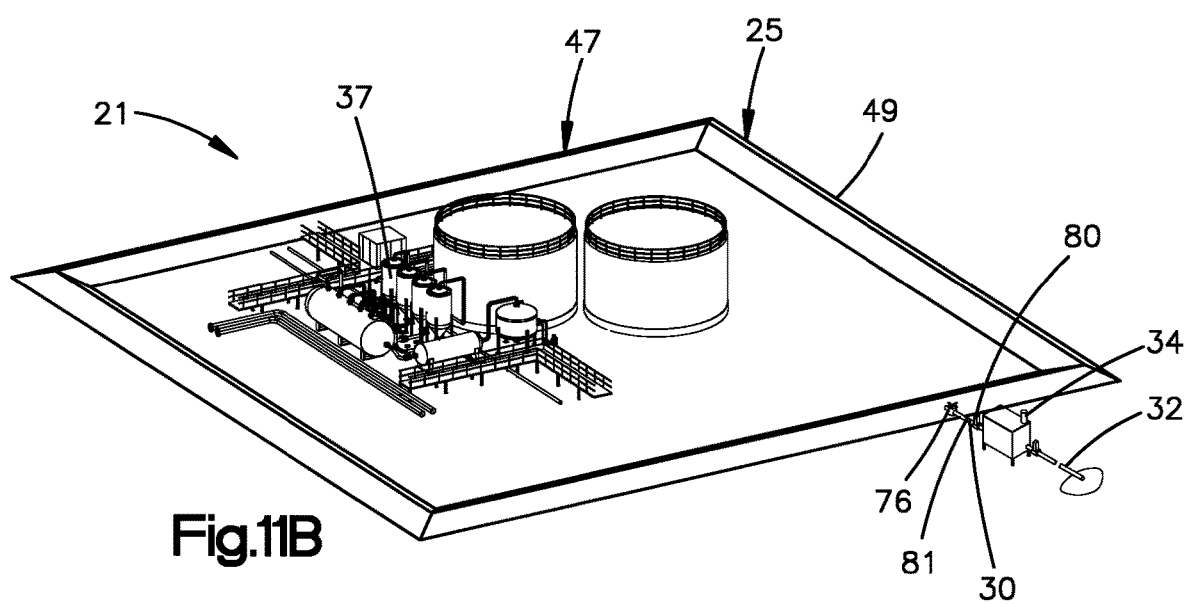
FIG. 11B is a schematic perspective view of an oil processing facility including a containment area and the monitoring system operatively coupled to the containment area.
Figure 11C:
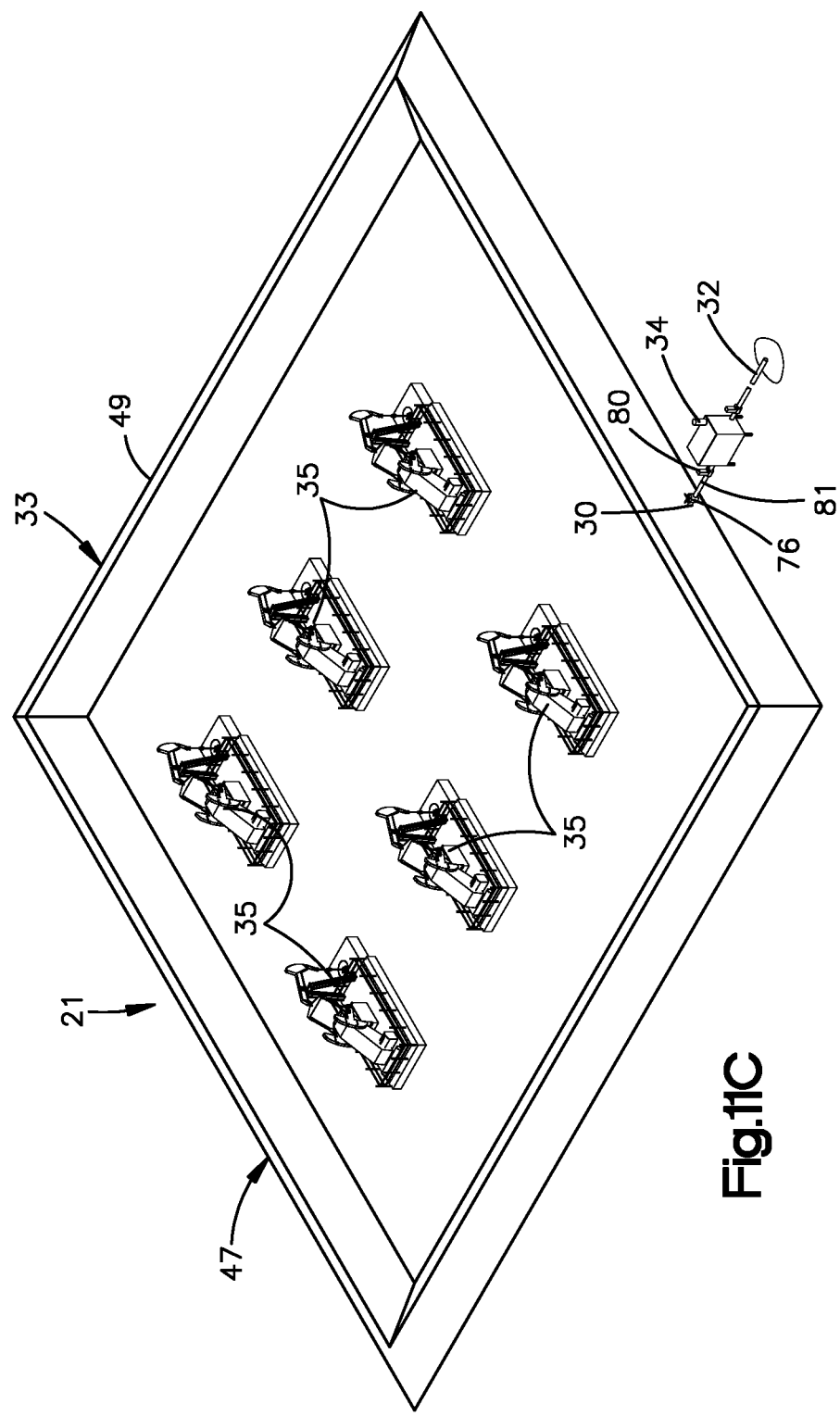
FIG. 11C is a schematic perspective view of an oil mining facility including a containment area and the monitoring system operatively coupled to the containment area.

Referring now to FIGS. 11A-11C, and as described above, the monitoring system 20 is configured to detect the presence of the selected group of hydrocarbons in a fluid 22 to be discharged from any desirable location of an oil handling facility 21. The oil handling facility 21 can be in the form of at least one of a petroleum storage facility 23, an oil processing facility 25, such as a refinery 37, and an oil mining facility 33 that includes one or more oil wells 35. Oil handling facilities can include containment areas 47, such as dikes 49, that are configured to contain fluids 22 such as storm water run off that may be contaminated with hydrocarbons, and thus not suitable to be introduced into the ambient environment. Such containment areas are typically lined with an impervious barrier to prevent the seepage of the contained fluids into the earth. It is desired to discharge the fluids from the containment area to a location outside the oil handling facility, where they are often returned to the earth. However, it is desired to ensure that the fluids being discharged do not contain environmentally harmful levels of hydrocarbons. Thus, the location of the oil handling facility can be configured as a containment area. The containment area 47 can surround individual oil handling apparatus, such as individual petroleum storage tanks 26 or individual oil wells 35. Alternatively, the containment area can surround a plurality of oil handling apparatus, such as a plurality of petroleum storage tanks 26 or a plurality of oil wells 35.

The monitoring system 20 can include the oil handling facility, including one or more of the petroleum storage facility 23, including the petroleum storage tank, the oil processing facility 25, and the oil mining facility 33. The monitoring system can further include the fluid flow separation chamber 28, the first or an inlet conduit 30 that extends from the containment area 47 of the oil handling facility to an inlet 29 (see FIG. 5A) of the fluid flow separation chamber 28. For instance, the inlet conduit 30 can be in fluid communication with a drain that extends through the dike 49 and into the containment area 47, such that fluid disposed in the containment area 47 can flow into the inlet conduit 30. The drain can be a side drain that extends through the side wall of the dike 49. For instance, the side drain can be located at a lower end of the side wall of the dike 49. Alternatively, the drain can be a bottom drain that causes fluid accumulated in the containment area 47 to flow through the bottom drain and into the inlet conduit 30. As discussed above, the fluid disposed in the containment area 47 can be storm water run off from the various apparatus of the oil handling facility that is surrounded by the dike 49. The monitoring system 20 can include a pump as desired to induce pressure that drives the fluid to flow from the containment area 47 into the inlet conduit 30. The inlet conduit 30 is configured to deliver the fluid 22 that is discharged from the containment area 47 to the fluid flow separation chamber 28, as described above, and into the ambient environment when the sensor does not detect the threshold presence of petroleum in the fluid.

Figure 12A:
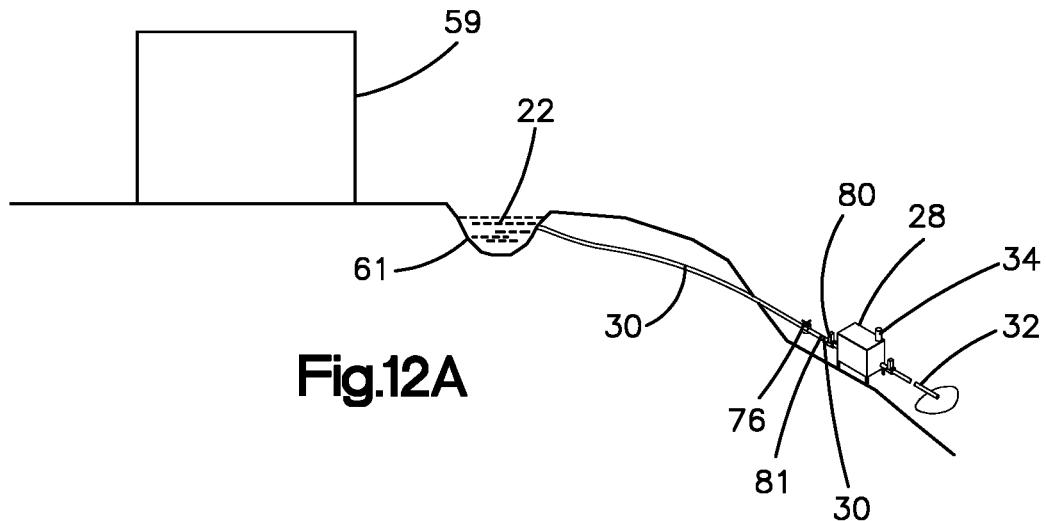
FIG. 12A is a schematic side elevation view of a retention pond, showing the monitoring system operatively coupled to the retention pond in accordance with one embodiment.
Figure 12B:
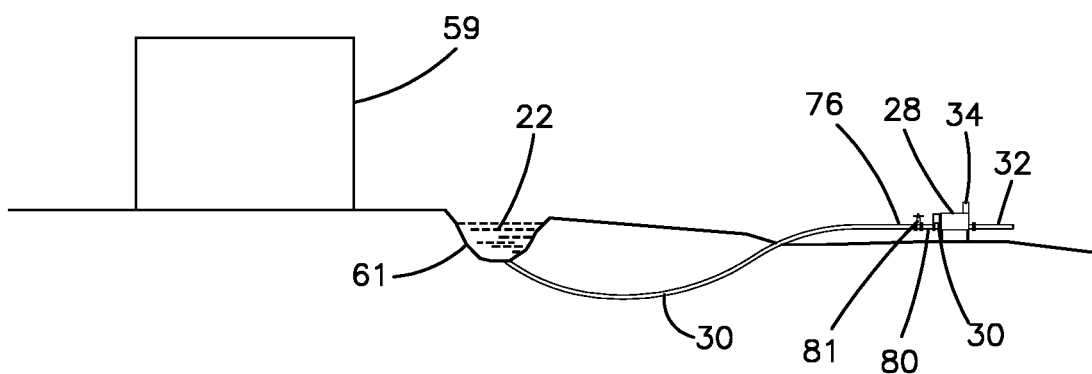
FIG. 12B is a schematic side elevation view of the retention pond illustrated in FIG. 12A, but showing the monitoring system operatively coupled to the retention pond in accordance with another embodiment.

Referring now to FIGS. 12A-B, it is recognized that oil handling facilities can often include a storm water run off retention pond 61. The storm water run off retention pond 61 is positioned to receive run off from various apparatus of the oil handling facility 10. For instance, when the retention pond 61 is disposed in the containment area 47, the run off can flow from the oil handling facility into the retention pond in the containment area 47, for instance under gravitational forces. In this regard, the retention pond 61 can be disposed at a sufficiently low elevation such that run off is directed into the retention pond 61 under gravitational forces. It is recognized that retention ponds 61 can exist outside the containment area 47, so long as they are sufficiently sealed to prevent the flow of the fluid contained in the retention pond 61 from traveling into the ambient environment. Thus, whether the retention pond 61 is disposed inside our out of the containment area 47, the retention pond 61 can be sealed from the soil to prevent potentially contaminated run off from entering the groundwater. The monitoring system 20 can further include the fluid flow separation chamber 28, the first or an inlet conduit 30 that extends from the retention pond 61 of the oil handling facility to the inlet 29 (see FIG. 5A) of the fluid flow separation chamber 28. For instance, the inlet conduit 30 can be in fluid communication with a drain that is in fluid communication with the retention pond 61, such that fluid disposed in the retention pond 61 can flow into the inlet conduit 30. As discussed above, the fluid disposed in the retention pond 61 can be storm water run off from the various apparatus of the oil handling facility. Thus, the location of the oil handling facility can be configured as the retention pond 61. The inlet conduit 30 is configured to deliver the fluid 22 that is discharged from the containment area 47 to the fluid flow separation chamber 28, as described above.

As illustrated in FIG. 12A in particular, the fluid flow separation chamber 28 can be disposed at a lower elevation than the drain of the retention pond 61. Accordingly, fluid in the retention pond 61 can flow from the retention pond 61 through the drain and into the fluid flow separation chamber 28 under gravitational forces. In accordance with this embodiment, the drain can be disposed at an upper end of the retention pond 61. As a result, the drain is positioned such that the fluid level in the retention pond 61 is unlikely to reside above the drain. When the fluid level in the retention pond 61 rises to the level of the drain, fluid can cascade through the drain and flow through the inlet conduit 30 and into and into the fluid flow separation chamber 28 under gravitational forces. A portion up to all of the inlet conduit 30 can extend along the ground, or can be buried underground. Alternatively or additionally, a pump can be induce a pressure that forces the fluid in the retention pond 61 to flow into the inlet conduit 30 and into the fluid flow separation chamber 28. The pump can be disposed in the inlet conduit 30 or in the retention pond 61. It may be desirable, for instance, to empty the retention pond 61. Thus, the pump can draw the fluid from an input conduit that has a free end proximate to the base of the retention pond 61. Further, it may be desirable to operate the pump during normal operation of the monitoring system 20. Alternatively or additionally still, a fluid flow regulator can limit the volumetric flow rate of the fluid that travels from the retention pond 61 to the fluid flow separation chamber 28.

Alternatively, as illustrated in FIG. 12B, the drain of the retention pond 61 can be a bottom drain, and thus disposed at the bottom of the retention pond 61. As a result, the drain is positioned such that as fluid 22 accumulates within the retention pond 61, the fluid flows through the bottom drain. It is envisioned that the fluid 22 can rise to a level above the drain in some circumstances. For instance, storm water run off can accumulate in the retention pond 61 at a rate faster than the rate at which storm water flows through the monitoring system 20. Thus, the fluid 22 in the retention pond 61 provides a fluid pressure that urges the fluid to flow out the drain, through the inlet conduit 30, and into the fluid flow separation chamber 28 as described above. It is understood that it may be desirable to regulate the flow of fluid to prevent the fluid pressure from causing the fluid 22 to flow at undesirably high volumetric flow rates into the fluid flow separation chamber. For instance, the fluid flow separation chamber 28 can be positioned at a higher elevation than that of the drain. In one example, the fluid flow separation chamber 28 can be positioned at a higher elevation than that of the retention pond 61. Accordingly, gravitational forces acting on the fluid 22 in the retention pond 61 can create pressure in the fluid 22 that causes the fluid 22 to travel through the inlet conduit 30 and through the fluid flow separation chamber 28. Alternatively or additionally, a pump can be disposed in the inlet conduit 30 or in the retention pond 61 that induces a pressure forcing the fluid in the retention pond 61 to flow into the inlet conduit 30 and into the fluid flow separation chamber 28. It may be desirable, for instance, to empty the retention pond 61. The pump can thereby draw the fluid from an input conduit that has a free end proximate to the base of the retention pond 61. Further, it may be desirable to operate the pump during normal operation of the monitoring system 20. Alternatively or additionally still, a fluid flow regulator can limit the volumetric flow rate of the fluid that travels from the retention pond 61 to the fluid flow separation chamber 28. It should be appreciated that one or both of the pump and the fluid flow regulator can also be present in the monitoring system 20 when the monitoring system 20 drains fluid from the roof of the storage tank in the manner described above.

Referring to FIGS. 2-12B in general, it should be appreciated that a method can be provided for assembling the monitoring system 20. The method can include the step of installing the first or automatic inlet valve 80 in the first or inlet conduit 30 that extends between the oil handling facility and a location external of the oil handling facility. In one example, the first or inlet conduit 30 can extend between the drain 44 in the floating roof 24 and a location external of the storage tank 26. In another example, the first or inlet conduit 30 can extend between a containment area and a location external of the containment area. In still another example, the first or inlet conduit 30 can extend between a fluid retention pond and a location remote from the fluid retention pond. As described above, the inlet valve 80 is configured to selectively permit and prevent fluid from flowing through the first conduit past the valve 80. The method can further include the step of attaching the inlet conduit 30 to the inlet 29 of the fluid flow separation chamber 28. The method can further include the step of placing the hydrocarbon sensor 34 in operative communication with the interior 54 of the fluid flow separation chamber 28 at a location proximate to the outlet 31, such that the sensor 34 is configured to sense a presence of hydrocarbons at the location proximate to the outlet 31. For instance, the hydrocarbon sensor 34 can be aimed so as to detect hydrocarbons in the form of a sheen on the top surface of the fluid.

The method can further include the step of installing the second or automatic outlet valve 86 in the second or outlet conduit 32 that extends out from the outlet 31 of the separation chamber 28. The automatic outlet valve 86 is configured to selectively permit and prevent the fluid 22 from flowing through the outlet conduit 32 past the outlet valve 86. The method can further include the step of installing a feedback mechanism that is configured to cause the inlet valve 80 to close in response to sensed petroleum at the sensor 34. The feedback mechanism can further be configured to cause the outlet valve 86 to close in response to sensed petroleum at the sensor 34. The feedback mechanism can be further configured to activate at least one of the audio alarm 62, the visual alarm 64, and the remote alarm signal 66. The feedback mechanism can be in the form of a controller or other like apparatus that receives an indication from the sensor that the presence of hydrocarbons has been detected.

The method can further include the step of placing the absorbent media 68 in at least one of the fluid flow channels 56 of the separation chamber 28. The method can further include the step of placing a plurality of the absorbent media 68 in a corresponding plurality up to all of the fluid flow channels 56 of the separation chamber 28. For instance, the method can include the step of encasing the absorbent media 68 in the water permeable cage 72. The method can further include the step of installing the P-trap in the outlet conduit 32 at a location downstream of the outlet 31 of the separation chamber 28 with respect to the fluid flow. The method can further include the step of attaching a drainage tube to the P-trap. The method can further include the step of mounting the at least one magnet 74 to the separation chamber 28 at a location in at least one of the fluid flow channels 56. The method can further include the step of attaching the bypass conduit 92 to the inlet conduit 30 at a location upstream of the inlet valve 80 with respect to fluid flow, so as to selectively direct the fluid 22 to flow from the inlet conduit 30 to the bypass conduit 92 when the inlet valve 80 is in the closed position.

With continuing reference to FIGS. 1-12B generally, it should be appreciated that a method can be provided for monitoring for a presence of hydrocarbons in the fluid 22 drained from a location of an oil handling facility. The method can include the step of directing the fluid 22 from the location of an oil handling facility and into the fluid flow separation chamber 28. In one example, the location of the oil handling facility is a storage tank 26, and in particular the floating roof 24. Thus, the directing step can include the step of directing the fluid from the floating roof 24 through the drain 44 and into the fluid flow separation chamber 28, for instance through the inlet 29. In another example, the location of the oil handling facility is a containment area, and the directing step can include the step of directing the fluid from the containment area, through the dike, and into the fluid flow separation chamber 28, for instance through the inlet 29. In still another example, the location of the oil handling facility is a retention pond, and the directing step can include the step of directing the fluid from the retention pond under gravitational forces or fluid pressure from fluid pressure in the pond, and into the fluid flow separation chamber 28, for instance through the inlet 29. The method can further include the step of causing the fluid 22 to flow from the inlet 29 of the fluid flow separation chamber 28 to the outlet 31 of the fluid flow separation chamber 28. The method can further include the step of sensing the fluid 22 proximate to the outlet 31 of the fluid flow separation chamber for the presence of hydrocarbons. When the sensing step detects the presence of a threshold amount of hydrocarbons in the fluid 22, the method can further include the step of closing the inlet valve 80 at a location between the roof 24 and the outlet 31 of the fluid flow separation chamber 28, thereby preventing further flow of the fluid 22 from the oil handling facility to the outlet 31 of the fluid flow separation chamber 28.

During the directing step, the fluid 22 can flow from the location of the oil handling facility to the fluid flow separation chamber 28 at a first velocity, and during the causing step, the fluid 22 can flow through the fluid flow separation chamber 28 at a second velocity less than the first velocity. For instance, the method can further include the step of, in the fluid flow separation chamber 28, converting a turbulent flow of the fluid 22 entering the inlet 29 of the fluid flow separation chamber 28 to a laminar flow at the outlet 31 of the fluid flow separation chamber 28. Therefore, the method can further include the step of, in the fluid flow separation chamber 28, causing a quantity of hydrocarbons present in the fluid 22 to rise to an upper surface of the fluid 22 disposed in the fluid flow separation chamber 28, for instance as a sheen. The causing step can further include the step of directing the fluid 22 sequentially through the plurality of channels 56 in respective opposite directions. The fluid 22 in the fluid flow separation chamber 28 can extend from the base 40 of the separation chamber 28 to an upper surface of the fluid 22 along a vertical direction, and the opposite directions are perpendicular to the vertical direction.

The causing step can include the step of causing the fluid 22 to flow in the fluid flow separation chamber 28 in a first one of the fluid flow channels 56 along a first longitudinal direction that is perpendicular to each of the lateral direction A and the vertical direction, and sequentially in a second one of the fluid flow channels 56 along a second longitudinal direction that is opposite the first longitudinal direction. The causing step further can further include the step of causing the fluid to travel along the lateral direction A from the first one of the fluid flow channels 56 to the second one of the fluid flow channels 56. When the sensing step detects the presence of the threshold amount of hydrocarbons in the fluid 22, the method can further include the step of activating an alarm state indicating the presence of the threshold amount of hydrocarbons in the fluid 22. For instance, the activating step can include at least one of activating the audio alarm 62, activating the visual alarm 64, and sending an alarm signal to a remote location.

When the sensing step detects the presence of the threshold amount of hydrocarbons in the fluid 22, the method can include the step of closing the inlet valve 80 at a location upstream of the outlet 31 of the fluid flow separation chamber 28 with respect to the direction of fluid flow, thereby preventing further flow of the fluid 22 from the floating roof 24 to the outlet 31 of the fluid flow separation chamber 28. For instance, the method can include the step of closing the inlet valve 80 at a location upstream of the inlet 29 of the fluid flow separation chamber 28 with respect to the direction of fluid flow, thereby preventing further flow of the fluid 22 from the floating roof 24 to the inlet 29 of the fluid flow separation chamber 28. Further, when the sensing step detects the presence of the threshold amount of hydrocarbons in the fluid 22, the method can include the step of closing the outlet valve 86 at a location downstream of the outlet 31 of the fluid flow separation chamber 28 with respect to the direction of fluid flow, thereby preventing further flow of the fluid 22 from the location of the oil handling facility to the outlet 31 of the fluid flow separation chamber 28.

The method can further include the step of directing the fluid 22 from the outlet 31 of the separation chamber through the P-trap. The method can further include the step of causing a volume of the fluid 22 to flow into the P-trap that is at least equal to a volume of the fluid 22 disposed between the inlet valve 80 and the P-trap when the inlet valve 80 is closed. The method can further include the step of draining the fluid from the P-trap after the outlet valve 86 has been closed. The method can further include the step of directing the fluid 22 to the bypass conduit 92 at a location upstream of the inlet valve 80 once the inlet valve 80 has been closed.

The causing step can include the step of causing the fluid 22 to flow through the absorbent media in the separation chamber 28 at a location upstream from the sensor 34. The causing step can further include the step of causing the fluid 22 to flow over the at least one magnet 74 that is configured to attach to ferrous particulates from the storm water-based fluid 22 in the separator chamber 28.

Further, a method can be provided for installing the monitoring system 20. The method can include the steps of installing the first or automatic valve 80 in the first or inlet conduit 30. The inlet conduit 30 can extend from a drain that is open to an interior of the containment area 47 that is contained by a dike. The drain can extend through the dike, or can extend over or under the dike. Alternatively, the inlet conduit 30 can extend from a drain of the retention pond 61. The valve 80 can be configured to selectively permit and prevent fluid from flowing through the first conduit past 30 the valve 80. The method can further include the step of attaching the first conduit 30 to the inlet 29 of the fluid flow separation chamber 28. The method can further include the step of placing the hydrocarbon sensor 34 in operative communication with the interior 54 of the fluid flow separation chamber 28 at a location proximate to the outlet 31, such that the sensor 34 is configured to sense a presence of hydrocarbons at the location proximate to the outlet 31. As described above, the sensor 34 is configured to sense the presence of hydrocarbons that are among a group of hydrocarbons that includes diesel/fuel oil, lube oil, motor oil, hydraulic oil, jet fuel, mineral oil, and crude oil. For instance, the hydrocarbon sensor 34 can be aimed so as to detect hydrocarbons in the form of a sheen on the top surface of the fluid.

The method can further include the step of installing the second or automatic outlet valve 86 in the second or outlet conduit 32 that extends out from the outlet 31 of the separation chamber 28. The second valve 86 is configured to selectively permit and prevent fluid from flowing through the second conduit 32 past the second valve 86, as described above. The method can further include the step of installing a feedback mechanism that is configured to cause the inlet valve 80 to close in response to sensed petroleum at the sensor 34. The feedback mechanism can further be configured to cause the outlet valve 86 to close in response to sensed petroleum at the sensor 34. The feedback mechanism can be further configured to activate at least one of the audio alarm 62, the visual alarm 64, and the remote alarm signal 66. The feedback mechanism can be in the form of a controller or other like apparatus that receives an indication from the sensor that the presence of hydrocarbons has been detected.

The method can further include the step of placing the absorbent media 68 in at least one of the fluid flow channels 56 of the separation chamber 28. For instance, the method can include the step of encasing the absorbent media 68 in the water permeable cage 72. The method can further include the step of installing the P-trap in the outlet conduit 32 at a location downstream of the outlet 31 of the separation chamber 28 with respect to the fluid flow. The method can further include the step of attaching a drainage tube to the P-trap. The method can further include the step of mounting the at least one magnet 74 to the separation chamber 28 at a location in at least one of the fluid flow channels 56. The method can further include the step of attaching the bypass conduit 92 to the inlet conduit 30 at a location upstream of the inlet valve 80 with respect to fluid flow, so as to selectively direct the fluid 22 to flow from the inlet conduit 30 to the bypass conduit 92 when the inlet valve 80 is in the closed position.

In another example, the oil handling facility can have a plurality of pumps and associated floats that cause the pumps to operate when the floats have reached a predetermined level, indicative of a potential flood condition. Operation of the pump can drain the accumulated fluid. Certain situations that can cause the floats to raise to the predetermined level include the presence of rainwater or runoff water. Accordingly, the separation chamber 28 can be attached to the outlet of the pump so as to allow the drainage of the liquid when the threshold amount of hydrocarbons is detected, but prevent the drainage when the threshold amount of hydrocarbons is not detected.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

What is claimed:

1. A method of monitoring for a presence of hydrocarbons among group of hydrocarbons in a fluid discharged from a location of an oil handling facility, the group of hydrocarbons including diesel/fuel oil, lube oil, motor oil, hydraulic oil, jet fuel, mineral oil, and crude oil, the method comprising the steps of:
   directing a fluid from the location of the oil handling facility and into a fluid flow separation chamber;
   causing the fluid to flow from an inlet of the fluid flow separation chamber to an outlet of the fluid flow separation chamber;
   sensing the fluid proximate to the outlet of the fluid flow separation chamber for the presence of the hydrocarbons while the fluid is permitted to flow through an open valve that is disposed at a location between the location of the oil handling facility and the outlet of the fluid flow separation chamber; and
   when the sensing step detects the presence of a threshold amount of the hydrocarbons in the fluid, closing the open valve, thereby preventing further flow of the fluid from the location of the oil handling facility to the outlet of the fluid flow separation chamber.

2. The method as recited in claim 1, wherein the sensing step comprises sensing a sheen on an upper surface of the fluid, and the threshold amount defines the sheen.

3. The method as recited in claim 1, wherein during the directing step, the fluid flows from the oil handling facility to the fluid flow separation chamber at a first velocity, and during the causing step, the fluid flows through the fluid flow separation chamber at a second velocity less than the first velocity.

4. The method as recited in claim 1, further comprising the step of, in the fluid flow separation chamber, causing a quantity of the hydrocarbons present in the fluid to rise to an upper surface of the fluid disposed in the fluid flow separation chamber.

5. The method as recited in claim 1, wherein the causing step further comprises directing the fluid sequentially through a plurality of channels in respective opposite horizontal directions.

6. The method as recited in claim 5, wherein the causing step comprises causing the fluid to flow in the fluid flow separation chamber in 1) a first one of the channels along a first longitudinal direction that is perpendicular to each of a lateral direction and the vertical direction, 2) sequentially in a second one of the channels along a second longitudinal direction that is opposite the first longitudinal direction, and 3) along the lateral direction from the first one of the channels to the second one of the channels.

7. The method as recited in claim 1, wherein when the sensing step detects the presence of the threshold amount of the hydrocarbons in the fluid, the method further comprises the step of closing at least one of 1) an inlet valve at a location upstream of the outlet of the fluid flow separation chamber with respect to the direction of fluid flow, thereby preventing further flow of the fluid from the oil handling facility to the outlet of the fluid flow separation chamber, and 2) an outlet valve at a location downstream of the outlet of the fluid flow separation chamber with respect to the direction of fluid flow, thereby preventing further flow of the fluid from the oil handling facility to the outlet of the fluid flow separation chamber.

8. The method as recited in claim 7, further comprising the step of directing the fluid from the outlet of the separation chamber into a P-trap.

9. The method as recited in claim 7, further comprising the step of directing the fluid to a bypass conduit at a location upstream of the inlet valve once the inlet valve has been closed.

10. The method as recited in claim 1, wherein the causing step further comprises causing the fluid to flow through an absorbent media in the separation chamber at a location upstream from the sensor, the absorbent media configured to absorb oil.

11. The method as recited in claim 1, wherein the causing step further comprises causing the fluid to flow over at least one magnet that is configured to entrap ferrous particulates from the storm water-based fluid in the separator chamber.

12. The method as recited in claim 1, wherein the oil handling facility is a petroleum storage facility, the location of the oil handling facility comprises a petroleum storage tank, and the directing step comprises directing the fluid from a floating roof of the petroleum storage tank, through a drain, and into a fluid flow separation chamber.

13. The method as recited in claim 1, wherein the location of the oil handling facility comprises a dike, and the directing step comprises directing the fluid through the dike.

14. The method as recited in claim 1, wherein the location of the oil handling facility comprises a retention pond, and the directing step comprises directing the fluid through a drain of the retention pond.

15. A fluid flow separation chamber configured to cause petroleum in a fluid to rise to an upper surface of the fluid, the fluid flow separation chamber comprising:
a chamber body having a base, and at least one outer wall that extends up from the base;
a plurality of baffles that extend up from the base, such that adjacent ones of the baffles define respective fluid flow channels, wherein each of the plurality of baffles extends from the at least one outer wall at a first end, and define a respective gap at a second end opposite the first end, such that the gaps are aligned with each other along a plane that is parallel to the base;
an inlet that extends through the body, wherein the fluid flow separation chamber is configured to receive the fluid through the inlet; and
an outlet that extends through the at least one outer wall below a midpoint of the at least one outer wall and at a location downstream of the inlet with respect to the direction of fluid flow through the fluid flow separation chamber, wherein the fluid flow separation chamber is configured to expel the fluid through the outlet without expelling the fluid through the at least one outer wall above the midpoint of the at least one outer wall.

16. The fluid flow separation chamber as recited in claim 15, wherein the plurality of baffles comprises:
a first set of at least one baffle that each extends from its respective first end to its respective second end in a first direction, whereby the first end of each of the first set of at least one baffle extends from the at least one outer wall, and the second end of each of the first set is spaced from the at least one outer wall so as to define a respective gap therebetween that is opposite its respective first end; and
a second set of at least one baffle that each extends from its respective first end to its respective second end in a second direction opposite the first direction, whereby the first end of each of the second set of at least one baffle extends from the at least one outer wall, and the second end of each of the second set is spaced from the at least one outer wall so as to define a respective gap therebetween that is opposite its respective first end.

17. The fluid flow separation chamber as recited in claim 16, further comprising an oil-absorbent media supported in at least one of the channels.

18. The fluid flow separation chamber as recited in claim 15, wherein the outlet defines a cross-sectional area that is substantially equal to a cross-sectional area of the inlet.

19. The fluid flow separation chamber as recited in claim 15, wherein the outlet is spaced above the base.

20. A monitoring system comprising:
the fluid flow separation chamber as recited in claim 15; and
a hydrocarbon sensor disposed proximate to the outlet of the fluid flow separation chamber, wherein the hydrocarbon sensor is configured to output a signal in response to a detection of a threshold amount of hydrocarbons of a group of hydrocarbons present in a fluid that travels through the fluid flow separation chamber along a direction from the inlet to the outlet, wherein the group of hydrocarbons includes diesel/fuel oil, lube oil, motor oil, hydraulic oil, jet fuel, mineral oil, and crude oil.

21. The fluid flow separation chamber as recited in claim 15, wherein the fluid flow separation chamber is configured to expel the fluid through the outlet without expelling the fluid or hydrocarbons through the at least one outer wall above the midpoint of the at least one outer wall.

\* \* \* \* \*

UNITED STATES PATENT AND TRADEMARK OFFICE
CERTIFICATE OF CORRECTION

| | | |
|---|---|---|
| PATENT NO. | : 10,571,447 B2 | Page 1 of 1 |
| APPLICATION NO. | : 15/135897 | |
| DATED | : February 25, 2020 | |
| INVENTOR(S) | : Rauch et al. | |

It is certified that error appears in the above-identified patent and that said Letters Patent is hereby corrected as shown below:

On the Title Page

Insert the following:
--(73) Assignee: EnviroEye LLC, Houston, TX (US)--

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*